(12) United States Patent
Miki

(10) Patent No.: US 9,244,072 B2
(45) Date of Patent: Jan. 26, 2016

(54) ANTI-HUMAN NOROVIRUS GII ANTIBODY

(75) Inventor: Motohiro Miki, Gosen (JP)

(73) Assignee: DENKA SEIKEN CO., LTD., Tokyo (JP)

(*) Notice: Subject to any disclaimer, the term of this patent is extended or adjusted under 35 U.S.C. 154(b) by 0 days.

(21) Appl. No.: 14/344,784

(22) PCT Filed: Sep. 13, 2012

(86) PCT No.: PCT/JP2012/073511
§ 371 (c)(1),
(2), (4) Date: Mar. 13, 2014

(87) PCT Pub. No.: WO2013/039165
PCT Pub. Date: Mar. 21, 2013

(65) Prior Publication Data
US 2014/0349277 A1 Nov. 27, 2014

(30) Foreign Application Priority Data
Sep. 13, 2011 (JP) ................. 2011-199059

(51) Int. Cl.
*G01N 33/577* (2006.01)
*C07K 16/10* (2006.01)
*G01N 33/569* (2006.01)

(52) U.S. Cl.
CPC .......... *G01N 33/56983* (2013.01); *C07K 16/10* (2013.01); *C07K 2317/34* (2013.01); *C07K 2317/55* (2013.01); *G01N 2333/08* (2013.01)

(58) Field of Classification Search
CPC ...... A61K 39/12; C07K 2317/55; C07K 7/06; C07K 14/08
See application file for complete search history.

(56) References Cited

U.S. PATENT DOCUMENTS

| 7,955,792 B2 | 6/2011 | Kamata et al. | |
|---|---|---|---|
| 2004/0073006 A1 | 4/2004 | Kageyama et al. | |
| 2010/0215649 A1* | 8/2010 | Frye et al. | 424/133.1 |
| 2012/0020964 A1 | 1/2012 | Frye et al. | |

FOREIGN PATENT DOCUMENTS

| EP | 1 342 727 A1 | 9/2003 |
|---|---|---|
| JP | 2004 301684 | 10/2004 |
| JP | 2009 542715 | 12/2009 |
| WO | 02 40509 | 5/2002 |
| WO | WO 2008/005880 A2 | 1/2008 |

OTHER PUBLICATIONS

Shiota et al (Journal of Virology 81:12298-12306, 2007; in IDS).*
Hansman et al (Journal of Virology 86:3635-3646, published online Jan. 12, 2012; in IDS).*
Shiota, T. et al., "Characterization of a Broadly Reactive Monoclonal Antibody against Norovirus Genogroups I and II: Recognition of Novel Conformational Epitope", Journal of Virology, vol. 81, No. 22, pp. 12298 12306, (Nov. 2007).

Parker, T. et al., "Identification of Genogroup I and Genogroup II Broadly Reactie Epitopes on the Norovirus Capsid", Journal of Virology, vol. 79, No. 12, pp. 7402-7409, (Jun. 2005).
Lochridge, V.P. et al., "Epitopes in the P2 domain of Norovirus VP1 recognized by monoclonal antibodies that block cell interactions", Journal of General Virology, vol. 86, pp. 2799-2806, (2005).
Kitamoto, N. et al., "Cross-Reactivity among Several Recombinant Calicivirus Virus-Like Particles (VLPs) with Monoclonal Antibodies Obtained from Mice Immunized Orally with One Type of VLP", Journal of Clinical Microbiology, vol. 40, No. 7, pp. 2459-2465, (Jul. 2002).
Hale, A. D. et al, "Identification of an Epitope Common to Genogroup 1 'Norwalk-Like Viruses' ", Journal of Clinical Microbiology, vol. 38, No. 4, pp. 1656-1660, (Apr. 2000).
Hansman, G. S. et al., "Genetic and antigenic diversity among noroviruses", Journal of General Virology, vol. 87, pp. 909-919, (2006).
Zheng, D.P. et al., "Norovirus Classification and proposed strain nomenclature", Virology, vol. 346, pp. 312-323, (2006).
Hansman, G. S. et al., "Structural Basis for Broad Detection of Genogroup II Noroviruses by a Monoclonal Antibody that Binds to Site Occluded in the Viral Particle", Journal of Virology, vol. 86, No. 7, pp. 3635-3646, (Jan. 2012).
Li, X. et al., "Characterization of a cross-reactive monoclonal antibody against Norovirus genogroups I, II, III and V", Virus Research, vol. 151, pp. 142-147, (2010).
Yoda, T. et al., "Precise Characterization of Norovirus (Norwalk-Like Virus)-Specific Monoclonal Antibodies with Broad Reactivity", Journal of Clinical Microbiology, vol. 41, No. 6, pp. 2367-2371 (Jun. 2003).
Tanaka, T., The evaluation of the improved Norovirus antigen-detection EIA kit, Japanese Journal of Medicine and pharmaceutical Science, vol. 61, No. 1, pp. 93-98, (2009)( with English Abstract).

(Continued)

*Primary Examiner* — Bao Li
(74) *Attorney, Agent, or Firm* — Oblon, McClelland, Maier & Neustadt, L.L.P.

(57) ABSTRACT

An anti-human-norovirus GII antibody which responds to substantially all genotypes of the human noroviruses belonging to GII and which can comprehensively detect such human noroviruses GII. The anti-human-norovirus GII antibody that binds to at least one of epitopes which are contained in amino acid regions represented by the following formulas (1) and (2):

$$P\text{-}X^1\text{-}X^2\text{-}P\text{-}G\text{-}E \quad (1) \; (\text{SEQ ID NO: 2})$$

$$X^3\text{-}X^4\text{-}X^5\text{-}F\text{-}Y\text{-}X^6\text{-}L\text{-}X^7\text{-}P\text{-}X^8 \quad (2) \; (\text{SEQ ID NO: 3})$$

(wherein, $X^1$ represents L, V, N, T, S, M, or R; $X^2$ represents F, Y, or M; $X^3$ represents V or G; $X^4$ represents N or S; $X^5$ represents Q, P, or S; $X^6$ represents S, T, or I; $X^7$ represents A or S; and $X^8$ represents M or V), and of an epitope formed of amino acid 483 of the amino acid sequence represented by SEQ ID NO: 1, or an epitope formed of an amino acid corresponding to amino acid 483, the regions and the amino acids being present in the P domain of a capsid structural protein of a human norovirus GII.

17 Claims, 11 Drawing Sheets

(56) References Cited

OTHER PUBLICATIONS

Tanaka, T. et al., "The evaluation of Norovirus antigen rapid diagnostic kit, Quicknavi™-Noro", Japanese Journal of Medicine and Pharmaceutical Science, vol. 61, No. 5, (May 2009)(with English Abstract).

International Search Report Issued Nov. 6, 2012 in PCT/JP12/073511 Filed Sep. 13, 2012.

Written Opinion of the International Searching Authority Issued Nov. 6, 2012 in PCT/JP12/073511 Filed Sep. 13, 2011.

Extended Search Report issued Mar. 20, 2015, in European Patent Application No. 12831058.8.

Motohiro Miki, et al., "In silico 3D structure analysis accelerates the solution of a real viral structure and antibodies docking mechanism", Frontiers in Microbiology, vol. 3, Nov. 6, 2012, DOI: 1O.3389/fmicb.2012.00387, 6 pages.

* cited by examiner

Fig. 1-1

```
485 (G2/1)                    1:MKMASNDAAPSNDGAAGLVPEVNNEMMALEPVAGASIAAPLTGQNNVIDPWIRMNFVQAP 60
NG1 (G2/2)                    1:MKMASNDAAPSTDGAAGLVPEVNNEVMALEPVAGAALAAPLTGQNNVIIDPWIRANFVQAP 60
MK04 (G2/2)                   1:MKMASNDAAPSTDGAAGLVPESNNEVMALEPVAGAALAAPVTGQTNIIDPWIRANFVQAP 60
336 (G2/3)                    1:MKMASNDAAPSNDGAAGLVPESNNEVMALEPVAGAAIAAPVTGQTNIIDPWIMNNFVQAP 60
18-3 (G2/3)                   1:MKMASNDAAPSNDGAAGLVPEINNEAMALDPVAGAAIAAPLTGQQNIIDPWIMNNFVQAP 60
809                           1:MKMASNDAAPSNDGAAGLVPEINNEAMALDPVAGAAIAAPLTGQQNIIDPWIMNNFVQAP 60
104 (G2/4)                    1:MKMASNDANPSDGSTANLVPEVNNEVMALEPVVGAAIAAPVAGQQNVIDPWIRNNFVQAP 60
2006a (Aomori) (G2/4)         1:MKMASSDANPSDGSTANLVPEVNNEVMALEPVVGAAIAAPVAGQQNVIDPWIRNNFVQAP 60
2006b (Saga) (G2/4)           1:MKMASNDANPSDGSAANLVPEVNNEVMALEPVVGAAIAAPVAGQQNVIDPWIRNNFVQAP 60
2007a (G2/4)                  1:MKMASNDANPSDGSTANLVPEVNNEVMALEPVVGAAIAAPVAGQQNVIDPWIRNNFVQAP 60
2008a (Apeldoorn_317_NL_2007) 1:MKMASSDANPSDGSTANLVPEVNNEVMALEPVVGAAIAAPVAGQQNVIDPWIRNNFVQAP 60
2008a (MiyoshiG2-4)           1:MKMASSDANPSDGSAANLVPEVNNEVMALEPVVGAAIAAPVAGQQNVIDPWIRNNFVQAP 60
2009a (New)                   1:MKMASSDANPSDGSTANLVPEVNNEVMALEPVVGAAIAAPVAGQQNVIDPWIRNNFVQAP 60
754 (G2/5)                    1:MKMASNDATPSNDGAAGLVPESNNEAMALEPVVGASLAAPVTGQTNIIDPWIRTNFVQAP 60
445 (G2/6)                    1:MKMASNDAAPSNDGAANLVPEANNEVMALEPVVGASIAAPVVGQQNIIDPWIRENFVQAP 60
7k (G2/6)                     1:MKMASNDAAPSNDGAANLVPEANDEVMALEPVVGASIAAPVVGQQNIIDPWIRENFVQAP 60
U25 (G2/8)                    1:MKMASNDAAPSNDGAAGLVPEINHEVMAIEPVAGASLAAPVVGQLNIIDPWIRNNFVQAP 60
Viet026 (G2/10)               1:MKMASNDAAPSNDGAAGLVPESNNEVMALEPVAGASLAAPVTGQTNIIDPWIRMNFVQAP 60
76 (G2/12)                    1:MKMASNDAAPSNDGAAGLVPEANNETMALEPVAGASIAAPLTGQNNIIDPWIRLNFVQAP 60
47 (G2/14)                    1:MKMASNDAAPSNDGAASLVPEGINETMPLEPVAGASIAAPVAGQTNIIDPWIRTNFVQAP 60
Kamo8 (G2/15)                 1:MKMASNDAAPSNDGAAGLVPEVNNETMALEPVAGASIAAPLTGQNNVIDPWIRLNFVQAP 60
Alpha23 (G2/17)               1:MKMASNDAAPSTDGAGNLVPESQQEVLPLAPVAGAALAAPVVGQTNIIDPWIKENFVQAP 60
```

Fig. 1-2

```
485       (G2/1)                    61:NGEFTVSPRNSPGEILLNLELGPELNPFLAHLSRMYNGYAGGVEVQVLLAGNAFTAGKLV 120
NG1       (G2/2)                    61:NGEFTVSPRNAPGEVLLSLELGPELNPYLAHLARMYNGYAGGMEVQVMLAGNAFTAGKLV 120
MK04      (G2/2)                    61:NGEFTVSPRNAPGEVLLNLELGPELNPYLAHLARMYNGYAGGMEVQVMLAGNAFTAGKLV 120
336       (G2/3)                    61:GGEFTVSPRNSPGEVLLNLELGPEINPYLAHLARMYNGYAGGFEVQVVLAGNAFTAGKVI 120
18-3      (G2/3)                    61:GGEFTVSPRNSPGEVLLNLELGPEINPYLAHLARMYNGYAGGFEVQVVLAGNAFTAGKVI 120
809                                 61:GGEFTVSPRNSPGEVLLNLELGPEINPYLAHLARMYNGYAGGFEVQVVLAGNAFTAGKVI 120
104       (G2/4)                    61:GGEFTVSPRNAPGEILWSAPLGPDLNPYLSHLARMYNGYAGGFEVQVILAGNAFTAGKII 120
2006a (Aomori) (G2/4)               61:GGEFTVSPRNAPGEILWSAPLGPDLNPYLSHLARMYNSYAGGFEVQVILAGNAFTAGKII 120
2006b (Saga) (G2/4)                 61:GGEFTVSPRNAPGEILWSAPLGPDLNPYLSHLARMYNGYAGGFEVQVILAGNAFTAGKII 120
2007a     (G2/4)                    61:GGEFTVSPRNAPGEILWSAPLGPDLNPYLSHLARMYNGYAGGFEVQVILAGNAFTAGKII 120
2008a (Apeldoorn_317_NL_2007)       61:GGEFTVSPRNAPGEILWSAPLGPDLNPYLSHLARMYNGYAGGFEVQVILAGNAFTAGKII 120
2008a (MiyoshiG2-4)                 61:GGEFTVSPRNAPGEILWSAPLGPDLNPYLSHLARMYNGYAGGFEVQVILAGNAFTAGKII 120
2009a (New)                         61:GGEFTVSPRNAPGEILWSAPLGPDLNPYLSHLARMYNGYAGGMEVQVMLAGNAFTAGKII 120
754       (G2/5)                    61:NGEFTVSPRNSPGEIVNLELGPELNPYLAHLARMYNGYAGGMEVQVVLAGNAFTAGKII 120
445       (G2/6)                    61:NGEFTVSPRNSPGEMLLNLELGPELNPYLSHLSRMYNGYAGGMQVQVVLAGNAFTAGKII 120
7k        (G2/6)                    61:QGEFTVSPRNSPGEMLLNLELGPELNPYLSHLSRMYNGYAGGMQVQVVLAGNAFTAGKII 120
U25       (G2/8)                    61:AGEFTVSPRNAPGEFLLDLELGPELNPYLAHLARMYNGHAGGMEVQIVLAGNAFTAGKIL 120
Viet026   (G2/10)                   61:QGEFTVSPRNSPGEVLLNLELGPELNPYLAHLSRMYNGYAGGMEVQIMLAGNAFTAGKLI 120
76        (G2/12)                   61:NGEFTVSPRNSPGEVLLNLELGPELNPYLAHLSRMYNGYAGGVEVQVLLAGNAFTAGKLV 120
47        (G2/14)                   61:NGEFTVSPRNSPGEILLNLELGPDLNPYLAHLSRMYNGYAGGVEVQVLLAGNAFTAGKIL 120
Kamo8     (G2/15)                   61:NGEFTVSPRNSPGEILVNLELGPELNPYLAHLSRMYNGYAGGVEVQVLLAGNAFTAGKLV 120
Alpha23   (G2/17)                   61:QGEFTVSPKNSPGEILVNLELGPKLNPYLDHLSRMYNSYAGGIDVMVVLAGNAFTAGKVL 120
```

Fig. 1-3

```
485 (G2/1)            121:FAAIPPRFPIENLSPGQITMFPHVIIDVRTLEPVLLPLPDVRNNFFHYNQEPEPRMRLVA 180
NG1 (G2/2)            121:FAAVPPHFPVENLSPQQITMFPHVIIDVRTLEPVLLPLPDVRNNFFHYNQKDDPKMRIVA 180
MK04 (G2/2)           121:FAAVPPHFPVENLSPQQITMFPHVIIDVRTLEPVLLPLPDVRNNFFHYNQKDDPKMRIVA 180
336 (G2/3)            121:FAAIPPNFPIDNLSAAQITMCPHVIVDVRQLEPINLPMPDVRNNFFHYNQGSDSRLRLIA 180
18-3 (G2/3)           121:FAAIPPNFPIDNLSAAQITMCPHVIVDVRQLEPINLPMPDVRNNFFHYNQGSDSRLRLIA 180
809                   121:FAAIPPNFPIDNLSAAQITMCPHVIVDVRQLEPVNLPMPDVRNNFFHYNQGSDSRLRLIA 180
104 (G2/4)            121:FAAVPPNFPTEGLSPSPSQVTMFPHIIPLPDVRNNFYHYNQSNDSTIKLIA 180
2006a (Aomori) (G2/4) 121:FAAVPPNFPTEGLSPSPSQVTMFPHIIVDVRQLEPVLIPLPDVRNNFYHYNQSNDPTIKLIA 180
2006b (Saga) (G2/4)   121:FAAVPPNFPTEGLSPSPSQVTMFPHIIVDVRQLEPVLIPLPDVRNNFYHYNQSNDPTIKLIA 180
2007a (G2/4)          121:FAAVPPNFPTEGLSPSPSQVTMFPHIIVDVRQLEPVLIPLPDVRNNFYHYNQSNDPTIKLIA 180
2008a (Apeldoorn_317_NL_2007) 121:FAAVPPNFPTEGLSPSPSQVTMFPHIIVDVRQLEPVLIPLPDVRNNFYHYNQSNDPTIKLIA 180
2008a (MiyoshiG2-4)   121:FAAVPPNFPTEGLSPSPSQVTMFPHIIVDVRQLEPVLIPLPDVRNNFYHYNQSNDPTIKLIA 180
2009a (New)           121:FAAVPPNFPTEGLSPSPSQITMFPHVIDVRTLEPVLLPMPDVRSTLFHFNQKDEPKMRLVA 180
754 (G2/5)            121:FAAVPPYFPVENLSPSPSQITMFPHVIDVRTLEPVLLPMPDVRSTLFHFNQKDEPKMRLVA 180
445 (G2/6)            121:FAAVPPHFPVDNISAAQITMCPHVIDVRTLEPVLLPMPDVRSTLFHFNQKDEPKMRLVA 180
7k (G2/6)             121:FAAVPPHFPVDNISAAQITMCPHVVDVRQLEPVLLPMPDVLLPMPDIRNSFFHFIQRDEPKMRLVA 180
U25 (G2/8)            121:FAVIPPGFPYENLSPAQLTMCPHVVDVRQLEPILLPMPDIRNTFFHYNQSNGPKLRLVA 180
Viet026 (G2/10)       121:FAAVPPHFPIENLSPPQITMFPPQITMFPHVIDVRTLEPVLLPMPDIRNSFFHFIQRDEPKMRLVA 180
76 (G2/12)            121:FAAVPPHFPPLENISPGQITMFPHVIDVRTLEPVLLPLPDVRNNFFHYNQQNEPRMRLVA 180
47 (G2/14)            121:FAAIPPNFFLVDMISPAQITMLPHLIVDVRTLEPIMTPLPDVRNVFYHFNNQPQPRMRLVA 180
Kamo8 (G2/15)         121:FAAIPPHFPVDNLSPGQITMFPHVIDVRTLEPVLLPLPDVRNNFFHYNQQSDQRMRLIA 180
Alpha23 (G2/17)       121:IAAIPPNFPVEGVSASQATQFPHVIDVRTLDPVRLPLPDVRSTFFHYTNDTEPKMRLVI 180
```

Fig. 1-4

```
485 (G2/1)              181:MLYTPLRSNGSGDDVFTVSCRVLTRPSPDFDFNYLVPPTVESKTKPFTLPILTLTIGELSNS 240
NG1 (G2/2)              181:MLYTPLRSNGSGDDVFTVSCRVLTRPSPDFDFTYLVPPTVESKTKPFTLPILTLGELSNS 240
MK04 (G2/2)             181:MLYTPLRSNGSGDDVFTVSCRVLTRPSPDFDFTYLVPPTVESKTKPFTLPILTLGELSNS 240
336 (G2/3)              181:MLYTPLRANNSGDDVFTVSCRVLTRPSPDFSFNLVPPTVESKTKPFTLPILTISEMSNS 240
18-3 (G2/3)             181:MLYTPLRANNSGDDVFTVSCRVLTRPSPDFSFNLVPPTVESKTKLFTLPILTISEMSNS 240
809                     181:MLYTPLRANNSGDDVFTVSCRVLTRPSPDFSFNLVPPTVESKTKPFTLPILTISEMSNS 240
104 (G2/4)              181:MLYTPLRANNAGDDVFTVSCRVLTRPSPDFDFIFLVPPTVESRTKPFTVPILTVEEMSNS 240
2006a (Aomori) (G2/4)   181:MLYTPLRANNAGDDVFTVSCRVLTRPSPDFDFIFLVPPTVESRTKPFSVPILTVEEMTNS 240
2006b (Saga) (G2/4)     181:MLYTPLRANNAGEDVFTVSCRVLTRPSPDFDFIFLVPPTVESRTKPFTVPILTVEEMTNS 240
2007a (G2/4)            181:MLYTPLRANNAGDDVFTVSCRVLTRPSPDFDFIFLVPPTVESRTKPFTVPILTVEEMTNS 240
2008a (Apeldoorn_317_NL_2007) 181:MLYTPLRANNAGDDVFTVSCRVLTRPSPDFDFIFLVPPTVESRTKPFSVPILTVEEMTNS 240
2008a (Miyoshi G2-4)    181:MLYTPLRANNAGDDVFTVSCRVLTRPSPDFDFIFLVPPTVESRTKPFTVPILTVEEMTNS 240
2009a (New)             181:MLYTPLRANNAGDDVFTVSCRVLTRPSPDFDFIFLVPPTVESRTKPFSVPILTVEEMTNS 240
754 (G2/5)              181:MLYTPLRSNGSGDDVFTVSCRILTRPSPEFDFTYLVPPTVESKTKPFTLPVLTLGELSNS 240
445 (G2/6)              181:MLYTPLRA-NSGEDVFTVSCRVLTRPAPDFEFTFLVPPTVESKTKPFTLPILTLGELSNS 239
7k (G2/6)               181:MLYTPLRA-NSGEDVFTVSCRVLTRPAPDFEFTFLVPPTVESKTKPFTLPILTLGELSNS 239
U25 (G2/8)              181:MLYTPLRSNGSGDDVFTVSCRVLTRPSPDFEFNFLVPPSVESKTKAFTLPILKISEMTNS 240
Viet026 (G2/10)         181:MLYTPLRSNGSGDDVFTVSCRVLTRPTPDFDFTYLVPPTVESKSKPFFTLPILTLGELTNS 240
76 (G2/12)              181:MLYTPLRSNGSGDDVFTVSCRVLTRPSPDFDFNYLVPPTLESKTKPFTLPILTIGELTNS 240
47 (G2/14)              181:MLYTPLRSNGSGDDVFTVSCRVLTRPTPDFEFIYLVPPSVESKTKPFTLPILTISELTNS 240
Kamo8 (G2/15)           181:MLYTPLRSNGSGDDVFTVSCRVLTRPSPDFDFNYLVPPTVESKTKPFSVPVLTLNELTNS 240
Alpha23 (G2/17)         181:WLYTPLRTNGSGDDSFTVSGRILTRPSQDFEFAFLIPPTVETKTTPFSVPGFSVQEMSNS 240
```

Fig. 1-5

```
485 (G2/1)                    241:RFPAPIDELYTSPNEGLVVQPQNGRSTLDGELLGTTQLVPSNICSLRGRI--------------:290
NG1 (G2/2)                    241:RFPVSIDQMYTSPNEVISVQCQNGRCTLDGELQGTTQLQVSGICAFKGEV------------:290
MK04 (G2/2)                   241:RFPVSIDQMYTSPNEVISVQCQNGRCTLDGELQGTTQLQVSGICAFKGEV------------:290
336 (G2/3)                    241:RFPVPIDSLHTSPTESVVVQCQNGRVTLDGELMGTTQLLPSQICAFRGTLTRPTNRASDQ  :300
18-3 (G2/3)                   241:RFPVPIDSLHTSPTENIVVQCQNGRVTLDGELMGTTQLLPSQICAFRGTLTRPTSRASDQ  :300
809                           241:RFPVPIESLHTSPTENIVVQCQNGRVTLDGELMGTTQLLPSQICAFRGVLTRSTSRASDQ  :300
104 (G2/4)                    241:RFPIPLEKLYTGPSSAFVVQPQNGRCTTDGVLLGTTQLSAVNICTFRGDV------------:290
2006a (Aomori) (G2/4)         241:RFPIPLEKLFTGPSSAFVVQPQNGRCTTDGVLLGTTQLSPVNICTFRGDV------------:290
2006b (Saga) (G2/4)           241:RFPIPLEKLFTGPSGAFVVQPQNGRCTTDGVLLGTTQLSPVNICTFRGDV------------:290
2007a (G2/4)                  241:RFPIPLERLYTGPSSAFVVQPQNGRCTTDGVLLGTTQLSAVNICTFRGDV------------:290
2008a (Apeldoorn_317_NL_2007) 241:RFPIPLEKLFTGPSSAFVVQPQNGRCTTDGVLLGTTQLSPVNICTFRGDV------------:290
2008a (MiyoshiG2-4)           241:RFPIPLEKLFTGPSSAFVVQPQNGRCTTDGVLLGTTQLSPVNICTFRGDV------------:290
2009a (New)                   241:RFPIPLEKLFTGPSSTFVVQPQNGRVTLDGELLGTTQLQACNICSIRGKV------------:290
754 (G2/5)                    241:RFPLSIDEMVTSPNESIVVQPQNGRCTLDCTLQGTTQLVPTQICAFRGTLISQTARATDS  :299
445 (G2/6)                    240:RFPAAIDMLYADPNESIVVQPQNGRCTLDGTLQGTTQLVPTQICAFRGTLISQTARAADS  :299
7k (G2/6)                     240:RFPAAIDMLYTDPNESIVVQPQNGRCTLDGELQGTTQLQGTTQLVPVSICGFRGTL------:290
U25 (G2/8)                    241:RFPIPVDQMYTSRNENIVVQPQNGRVTLDGELQGTTTLQPVSICGFRGTL------------:290
Viet026 (G2/10)               241:RFPLPIDVLYTNPNESAIVQCQNGRCTLDGELQGTTQLLPTGICAFRGKV------------:290
76 (G2/12)                    241:RFPVPIDELYTSPNESLVVQPQNGRCALDGELQGTTQLLPTAICSFRGRI------------:290
47 (G2/14)                    241:RFPIPIEQLYTAPNETNVVQCQNGRCTLDGELQGTTQLLSSAVCFLQGR-------------:289
Kamo8 (G2/15)                 241:RFPVPIDAMYTSPNDSIVVQPQNGRATIDGELLGTTQLIPSGICSFRGKI------------:290
Alpha23 (G2/17)               241:RWPAAISAMVVRGNEPQVVQFQNGRAHLDGMLLGTTPVSPNYIASYRGISTGNSRSASSE  :300
```

Fig. 1-6

```
485 (G2/1)              291:NAHLPDNQH--RWNMQVTNANGTPFDPTEDVPAPLGTPDFLANIYGVTSQRN---PDNTC 345
NG1 (G2/2)              291:TAHLHDNDH--LYNVTITNLNGPPFDPSEDIPAPLGVPDFQGRVFGVISQRDKQNAAGHS 348
MK04 (G2/2)             291:TAHLHDNDH--LYNVTITNLNGSPFDPSEDIPAPLGVPDFQGRVFGVISQRDKHNSPGHN 348
336 (G2/3)              301:ADTATPRLFNHQWHIQLDNLNGTPYDPAEDIPAPLGTPDFRGKVFGVASQRD-PDGT--- 356
18-3 (G2/3)             301:ADTPTPRLFNHRWHIQLDNLNGTPYDPAEDIPAPLGTPDFRGKVFGVASQRN-PDST--- 356
809                     301:ADTATPRLFNYYWHVQLDNLNGTPYDPAEDIPGLGTPDFRGKVFGVASQRN-LDST--- 356
104 (G2/4)              291:-THIAGSHD---YTMNLASQNWSNYDPTEEIPAPLGTPDFVGKIQGMLTQ------TTR 339
2006a (Aomori) (G2/4)   291:-THIAGTQE---YTMNLASQNWNNYDPTEEIPAPLGTPDFVGKIQGVLTQ------TTR 339
2006b (Saga) (G2/4)     291:-THIAGSRN---YTMNLASLNWNNYDPTEEIPAPLGTPDFVGKIQGLLTQ------TTK 339
2007a (G2/4)            291:-THIAGSRN---YTMNLASQNWNNYDPTEEIPAPLGTPDFVGKIQGMLTQ------TTR 339
2008a (Apeldoorn_317_NL_2007) 291:-THITGSRN---YTMNLATQNWNSYDPTEEIPAPLGTPDFVGKIQGVLTQ------TTR 339
2008a (Miyoshi G2-4)    291:-AHIAGSRN---YTMNLAPLNWNNYDPTEEIPAPLGTPDFVGKIQGMLTQ------TTK 339
2009a (New)             291:-THIAGSRN---YTMNLASQNWNSYDPTEEIPAPLGTPDFVGKIQGVLTQ------TTR 339
754 (G2/5)              291:TGQVPSEQH--MWNLEITNLNGTQFDPTDDVPAPLGVPDFAGEVFGVLSQRNRGESNPAN 348
445 (G2/6)              300:TDSP-QRARDHPLHVQVKNLDCTQYDPTDDIPAVLGAIDFKGTVFGVASQRD-VSGPQEQ 357
7k (G2/6)               300:TDSP-QRARNHPLHVQVKNLDCTQYDPTDDIPAVLGAIDFKCTVFGVASQRD-VSGQQEQ 357
U25 (G2/8)              291:QTRLADQPN--YTYQVHLENLDGSPVDPTDEVPAPLGTPDFQAQLFGVISQR-------S 341
Viet026 (G2/10)         291:TQQVQDEHRGTHWNMTVTNLNGTPFDPTGDVPAPLGTPDFSGQIYGVISQRNTNTVPGEG 350
76 (G2/12)              291:NQKVSGENH--VWNMQVTNINGTPFDPTGDVPAPLGTPDFSGKLFGVLSQRD---HDNAC 345
47 (G2/14)              290:-TVADNGDNWDQNLLQLTYPNGASYDPTDEVPAPLGTQDFSGMLYGVLTQ----DNVNVS 344
Kamo8 (G2/15)           291:TTHLADDRKH--LWNIQVSNLNGTPFDPTDDVPAPLGMPDFSGQIFGVVSQRDTG-TNPAN 347
Alpha23 (G2/17)         301:ADERAVGSF-DVW-VRLQEPDGQPYDIFGKQPAPIGTPDFKAVIVGFAAR--------P 349
```

Fig. 1-7

```
485   (G2/1)             346:-----RAHDGILATWSPKFTPKLGSVVLGTWEDRDFDINQPT--RFTPVGLY---D----T 392
NG1   (G2/2)             349:E-PANRGHDAVVPTYTAQYTPKLGQVQIGTWQTDDLQVNQPV--KFTPVGL-------NDT 399
MK04  (G2/2)             349:E-PANRGHDAVVPTYTSQYTPKLGQIQIGTWQTDDLTVNQPV--KFTPVGL-------NDT 399
336   (G2/3)             357:-----TRAHEAKVDTTSGRFTPKLGSLEITT-ESDDFNQNKPT--RFTPVGI-----GVDNE 405
18-3  (G2/3)             357:-----TRAHEAKVDTTSGRFTPKLGSLEITT-ESDDFDTNQST--KFTPVGI-----GVDNE 405
809                      357:-----TRAHEAKVDTTAGRFTPKLGSLEIST-DSDDFDQNQPT--KFTPVGI-----GVDNE 405
104   (G2/4)             340:EDGSTRAHKATVSTGSVHFTPKLGSVQYTTDTNNDFQTGQNT--KFTPVGVIQDGN-NHQ 396
2006a (Aomori) (G2/4)    340:RDGSTRGHKATVSTGSVHFTPKLGRIQFSTDTSNDFETGQNT--RFTPVGVVQDGSTTHQ 397
2006b (Saga) (G2/4)      340:GDGSTRGHKATVYTGSAPFTPKLGSVQFSTDTENDFETHQNT--KFTPVGVIQDGSTTHR 397
2007a (G2/4)             340:SDGSTRGHKATVLTGSADFAPKLGRVQFATDTDNDFESGQNT--KFTPVGVIQDGSTTHR 397
2008a (Apeldoorn_317_NL_2007) 340:ADGSTRGHKATVYTGSADFAPKLGRVQFATDTDNDFDANQNT--KFTPVGVIQDGNTAHR 397
2008a (Miyoshi G2-4)     340:GDGSTRGHKATVYTGSADFTPKLGSVQFCTDTENDFETHQNT--KFTPVGVIQDGSTTHR 397
2009a (New)              340:TDGSTRGHKATVYTGSADFSPKLGRVQFATDTDNDFDANQNT--KFTPVGVIQDGGTAHR 397
754   (G2/5)             349:-----RAHDAVVATYSDKYTPKLGLVQIGTWNTND-VENQPT--KFTPIGLN---EVANG 397
445   (G2/6)             358:GHYATRAHEAHIDTTDPKYAFKLGTILIKS-ESNDFITNQPI--RFTPVGM-----G---D 407
7k    (G2/6)             358:GHYATRAHEAHIDTTDPKYAPKLGTILIKS-GSDDFNTNQPI--RFTPVGM-----G---D 407
U25   (G2/8)             342:SDNATRAHEARVNTNDPTFAPQIAQVRFKS-PSNDFFDNEPI--KFTPVGI-----SVDSQ 394
Vietο26 (G2/10)          351:NLPANRAHEAVIATYSPKFTPKLGNIQFSTWETQDVSSGQPT--KFTPVGLA---SVDAN 405
76    (G2/12)            346:-----RSHDAVIATNSAKFTPKLGAIQIGTWEEDDVHINQPT--KFTPVGLF----E---N 392
47    (G2/14)            345:TGEAKNAKGIYISTTSGKFTPKIGSIGLHS-ITEHVHPNQQS--RFTPVGV-----AVDEN 397
Kamo8 (G2/15)            348:-----RAHDAVLATYSAKYTPKLGSVQIGTWDTEDLLERQPV--KFTPVGLN---EIGQD 397
Alpha23 (G2/17)          350:LTSGSYANEAYVNTTASDYAPATGNMRFTVRNGGTGHISANKYWEFKSFGV--EGERHTN 407
```

Fig. 1-8

| | | |
|---|---|---|
| 485 (G2/1) | 393: DHFNQWALPNYSGALTLNMNLAPSVA P L FPGE QLLFFRSHIPL--KGGT--SNGAIDCLL | 448 |
| NG1 (G2/2) | 400: EHFNQWVVPRYAGALNLNTNLAPSVA P V FPGE RLLFFRSYIPL--KGGY--GNPAIDCLL | 455 |
| MK04 (G2/2) | 400: EHFNQWVVPRYAGALNLNTNLAPSVA P V FPGE RLLFFRSYIPL--KGGY--GNPAIDCLL | 455 |
| 336 (G2/3) | 406: ADFQQWILPDYSGQFTHNMNLAPAVA P N FPGE QLLFFRSQLPS--SGGR--SNGILDCLV | 461 |
| 18-3 (G2/3) | 406: AEFQQWSLPNYSGQFTHNMNLAPAVA P N FPGE QLLFFRSQLPS--SGGR--SNGVLDCLV | 461 |
| 809 | 406: AEFQQWSLPDYSGQFTHNMNLAPAVA P N FPGE QLLFFRSQLPS--SGGR--SNGVLDCLV | 461 |
| 104 (G2/4) | 397: NEPQQWVLPNYSGRTGHNVHLAPAVA P T FPGE QLLFFRSTMPG--CSGY--PNMNLDCLL | 452 |
| 2006a (Aomori) (G2/4) | 398: NEPQQWVLPNYSGRDSHNVHLAPAVA P S FPGE QLLFFRSTMPG--CSGY--PNMNLDCLL | 453 |
| 2006b (Saga) (G2/4) | 398: NEPQQWVLPSYSGRNVHNVHLAPAVA P T FPGE QLLFFRSTMPG--CSGY--PNMDLDCLL | 453 |
| 2007a (G2/4) | 398: NEPQQWVLPNYSGRTGHNVHLAPAVA P T YPGE QLLFFRSTMPG--CSGY--PNMDLDCLL | 453 |
| 2008a (Apeldoorn_317_NL_2007) | 398: NEPQQWVLPSYSGRNSHNVHLAPAVA P T FPGE QLLFFRSTMPG--CSGY--PNMDLDCLL | 453 |
| 2008a (Miyoshi G2-4) | 398: NEPQQWVLPSYSGRNVHNVHLAPAVA P N FPGE QLLFFRSTMPG--CSGY--PNMDLDCLL | 453 |
| 2009a (New) | 398: NEPQQWVLPSYSGRNTHNVHLAPAVA P T FPGE QLLFFRSTMPG--CSGY--PNMDLDCLL | 453 |
| 754 (G2/5) | 398: HRFEQWTLPRYSGALTLNMNLAPAVA P L FPGE RLLFFRSYVPL--KGGF--GNPAIDCSV | 453 |
| 445 (G2/6) | 408: NNWRQWELPDYSGRLTLNMNLAPAVS P S FPGE RILFFRSIVPS--AGGY--GSGYIDCLI | 463 |
| 7k (G2/6) | 408: NNWRQWELPDYSGRLTLNMNLAPAVS P S FPGE RILFFRSIVPS--AGGY--GSGYIDCLI | 463 |
| U25 (G2/8) | 395: NSYNQWLLPRYGGHLTNNTHLAPSVS P M FPGE QILFFRSFMPG--ASGH--TDGAIDCLL | 450 |
| Viet026 (G2/10) | 406: SHFDQWTLPSYSGALTLNMNLAPSVA P V FPGE CLLFFRSFIPL--KGGY--GNPAIDCLM | 461 |
| 76 (G2/12) | 393: EGFNQWTLPNYSGALTLNMGLAPPVA P T FPGE QILFFRSHIPL--KGGV--ADPVIDCLL | 448 |
| 47 (G2/14) | 398: TPFQQWVLPHYAGSLALNTNLAPAVA R L SLVS NCCSSGPVSHV--FKAYRGQDAFIDCLL | 455 |
| Kamo8 (G2/15) | 398: KHFDQWVLPNYSGALGLNMHLAPAVS P L FPGE RLLFFRSYIPL--KGGH--GDPFIDCLV | 453 |
| Alpha23 (G2/17) | 408: IQYQEYELPDYSGQVASNHNLAPPVA P R MPGE SLLLFQSSMPVWDDGHGESTPKKIHCLL | 467 |

Fig. 1-9

```
485    (G2/1)                   449: PQEWVQHFYQESAPSSTDVALIRYTNPDTGRVLF E AKLHRQGFITVANSGSRPIVVPPNG 508
NG1    (G2/2)                   456: PQEWVQHFYQEAAPSMSEVALVRYINPDTGRALF E AKLHRAGFVTVSSNTSAPVVVPANG 515
MK04   (G2/2)                   456: PQEWVQHFYQEAAPSMSEVALVRYINPDTGRALF E AKLHRAGFMTVSSNTSAPVVVPANG 515
336    (G2/3)                   462: PQEWVQHFYQESAPAQTQVALVRYVNPDTGRVLF E AKLHKMGFMTIAKNGDSPITVPPNG 521
18-3   (G2/3)                   462: PQEWVQHFYQESAPAQTQVALVKYVNPDTGRVLF E AKLHKLGFMTIAKNGDSPITVPPNG 521
809                             462: PQEWVQHFYQESAPAQTQVALVRYVNPDTGKVLF E AKLHKLGFMTIANNGDSPITVPPNG 521
104    (G2/4)                   453: PQEWVQHFCQEAAPAQSDVALLRFVNPDTGRVLF E CKLHKSGYVTVAHTGPHDLVIPPNG 512
2006a  (Aomori) (G2/4)          454: PQEWVQHFYQEAAPAQSDVALLRFVNPDTGRVLF E CKLHKSGYVTVAHTGQHDLVIPPNG 513
2006b  (Saga) (G2/4)            454: PQEWVQHFYQEAAPAQSDVALLRFVNPDTGRVLF E CKLHKSGYVTVAHTGQHDLVIPPNG 513
2007a  (G2/4)                   454: PQEWVQHFYQEAAPAQSDVALLRFVNPDTGRVLF E CKLHKSGYVTVAHTGQHDLVIPPNG 513
2008a  (Apeldoorn_317_NL_2007)  454: PQEWVQYFYQEAAPAQSDVALLRFVNPDTGRVLF E CKLHKSGYVTVAHTGQHDLVIPPNG 513
2008a  (MiyoshiG2-4)            454: PQEWVQHFYQEAAPAQSDVALLRFVNPDTGRVLF E CKLHKSGYVTVAHTGQHDLVIPPNG 513
2009a  (New)                    454: PQEWVQYFYQEAAPAQSDVALVRYVNPDTGRVLF E CKLHKSGYVTVAHTGQHDLVIPPNG 513
754    (G2/5)                   454: PQEWVQHFYQESAPSLGDVALVRYVNPDTGRVLF E AKLHKGGFLTVSSTSTGPVVVPANG 513
445    (G2/6)                   464: PQEWGQHFYQEAAPSQSAVALVRYVNPDTGRNIF E AKLHREGFLTVANSGNNPIVVPPNG 523
7k     (G2/6)                   464: PQEWVQHFYQEAAPSQSAVALVRYVNPDTGRNIF E AKLHREGFLTVANCGNNPIVVPPNG 523
U25    (G2/8)                   451: PQEWVAHFYQEAATAQTDVALIRFVNPDTGRVLF E GKLHKQGFITISNSGDHPIVMPANG 510
Viet026 (G2/10)                 462: PQEWVQHLYQESAPSLSDVALVRYVNPETGRTLF E AKLHRNGFLTVARNSAGPVVAPTNG 521
76     (G2/12)                  449: PQEWIQHLYQESAPSQSDVALIRFTNPDTGRVLF E AKLHRSGYITVANTGSRPIVVPANG 508
47     (G2/14)                  456: PQEWVNHFYQEAAPSQADVALIRYVNPDTGRTLF E AKLHRSGFITVSHTGAYPLVVPPNG 515
Kamo8  (G2/15)                  454: PQEWIQHFYQESAPAQSSVALLRYVNPDTGRTLF E AKLHKEGFITVSSTENRPIVVPPNG 513
Alpha23 (G2/17)                 468: PQEFIGHFFDKQAPSLGDAALLRYVNQETNRVLF E CKLYRDGYITVAASSGL-LDFPLDG 526
```

Fig. 1-10

| | | | | | | |
|---|---|---|---|---|---|---|
| 485 (G2/1) | 509: | YFRFDSW | V N | QF | YSL | APM | GTGNGRRRVQ--- | 535 |
| NG1 (G2/2) | 516: | YFRFDSW | V N | QF | YSL | APM | GAGNGRRRVQ--- | 542 |
| MK04 (G2/2) | 516: | YFRFDSW | V N | QF | YSL | APM | GTGNGRRRVQ--- | 542 |
| 336 (G2/3) | 522: | YFRFFESW | V N | PF | YTL | APM | GTGKGRRRIQ--- | 548 |
| 18-3 (G2/3) | 522: | YFRFESW | V N | PF | YTL | APM | GTGNGRRRIQ--- | 548 |
| 809 | 522: | YFRFESW | V N | PF | YTL | APM | GTGNGRRRIQ--- | 548 |
| 104 (G2/4) | 513: | YFRFDSW | V N | QF | YTL | APM | GNGAGRRRAL--- | 539 |
| 2006a (Aomori) (G2/4) | 514: | YFRFDSW | V N | QF | YTL | APM | GNGTGRRRAL--- | 540 |
| 2006b (Saga) (G2/4) | 514: | YFRFDSW | V N | QF | YTL | APM | GNGTGRRRAL--- | 540 |
| 2007a (G2/4) | 514: | YFRFDSW | V N | QF | YTL | APM | GNGTGRRRAV--- | 540 |
| 2008a (Apeldoorn_317_NL_2007) | 514: | YFRFDSW | V N | QF | YTL | APM | GNGTGRRRAL--- | 540 |
| 2008a (MiyoshiG2-4) | 514: | YFRFDSW | V N | QF | YTL | APV | GNGTGRRRVL--- | 540 |
| 2009a (New) | 514: | YFRFDSW | V N | QF | YTL | APM | GNGTGRRRAL--- | 540 |
| 754 (G2/5) | 514: | YFRFDSW | V N | QF | YSL | APM | GTGNGRRRVQ--- | 540 |
| 445 (G2/6) | 524: | YFRFEAW | V N | QF | YTL | APM | GSGQGRRRAX--- | 550 |
| 7k (G2/6) | 524: | YFRFEAW | G N | QF | YTL | APM | GSGQGRRRAQ--- | 550 |
| U25 (G2/8) | 511: | YFRFEAW | V N | QF | YSL | APV | GTGSGRRRIQ--- | 537 |
| Viet026 (G2/10) | 522: | YFRFDSW | V N | QF | YTL | APM | GNGSGRRRMQ--- | 548 |
| 76 (G2/12) | 509: | YFRFDTW | V N | QF | YSL | APM | GTGNGRRRVQ--- | 535 |
| 47 (G2/14) | 516: | HFRFDSW | V N | QF | YSL | APM | GTGNGRRRIQ--- | 542 |
| Kamo8 (G2/15) | 514: | YFRFDSW | V N | QF | YSL | APM | CTGNGRRRVQ--- | 540 |
| Alpha23 (G2/17) | 527: | FFRFDSW | V S | SF | YIL | SPV | GSGQGRRGRVRFQ | 556 |

…

ANTI-HUMAN NOROVIRUS GII ANTIBODY

CROSS REFERENCE TO RELATED APPLICATIONS

The present application is a 35 U.S.C. §371 national stage patent application of International patent application PCT/JP2012/073511, filed on Sep. 13, 2012, published as WO/2013/039165 on Mar. 21, 2013, the text of which is incorporated by reference, and claims the benefit of the filing date of Japanese application no. 2011-199059, filed on Sep. 13, 2011, the text of which is also incorporated by reference.

TECHNICAL FIELD

The present invention relates to an antibody to human norovirus GII and, more particularly, to an anti-human-norovirus GII antibody for detecting human norovirus GII in a specimen through an immunological assay.

BACKGROUND ART

When a human is orally infected with a human norovirus, the virus proliferates in the duodenum and the upper portion of the small intestine, thereby triggering infectious gastroenteritis. In this case, epithelial cells of the small intestine near the duodenum fall, thereby causing symptoms including vomiting, diarrhea, and abdominal pain. The incubation period from infection with norovirus to the onset is about 12 hours to 72 hours (average 1 to 2 days), and excretion of the virus to the feces lasts about 1 to 3 weeks even after the symptoms have disappeared. In some cases, such virus excretion for longer than 7 weeks is reported. About 70% of reported cases of food poisoning are caused by norovirus infection.

A norovirus is a virus having no envelope and having a plus single-stranded RNA of about 7,500 bases as the genome thereof. The genome of the norovirus is reported to include three protein coding regions (ORFs): ORF1, coding for a non-structural protein relating to viral replication; ORF2, coding for a capsid structural protein (VP1); and ORF3, coding for a minor structural protein (VP2). Also, the norovirus is categorized into 5 groups: Genogroups I to V (GI to GV), on the basis of similarity of capsid gene sequence. Of these, noroviruses GI, GII, and GIV are main causal viruses for human infection. In particular, Genogroup I (GI) and Genogroup II (GII) have a genetic diversity, and a variety of viruses having different phylogenetic properties are detected in specimens from humans. Thus, Genogroup I and Genogroup II may be divided into 14 or more genotypes and 17 or more genotypes, respectively.

Detection of norovirus is carried out by detecting a capsid structural protein with an antibody through enzyme immunoassay (EIA) (see Non-Patent Document 1) or immunochromatography (Non-Patent Document 2). Thus, correct detection of a human norovirus antigen requires an antibody that responds to all the genotypes.

However, hitherto, an antibody that can recognize and respond to a common antigen region has not been readily obtained. Thus, a norovirus detection reagent is produced through combination of a plurality of antibodies to norovirus antigen peptides having a specific amino acid sequence or to fragments thereof (see, for example, Patent Document 1), and noroviruses of different genotypes are individually detected.

Therefore, there is demand for creating an antibody that can comprehensively detect a wide variety of noroviruses GII of different genotypes.

CITATION LIST

Patent Document

Patent Document 1: JP-A-2009-542715

Non-Patent Documents

Non-Patent Document 1: "The Evaluation of Improved Norovirus Antigen-Detection EIA Kits," Japanese Journal of Medicine and Pharmaceutical Science (monthly) Vol. 61, No. 1, p. 93-98 (Jan. 25, 2009)
Non-Patent Document 2: "The evaluation of Norovirus antigen rapid diagnostic kit "Quicknavi-Noro"," Japanese Journal of Medicine and Pharmaceutical Science (monthly) Vol. 61, No. 5, p. 779-785 (May 25, 2009)

SUMMARY OF THE INVENTION

Problems to be Solved by the Invention

An object of the present invention is to provide an anti-human-norovirus GII antibody which responds to substantially all genotypes of the human noroviruses belonging to GII and which can comprehensively detect such human noroviruses GII.

Means for Solving the Problems

In order to attain the aforementioned object, the present inventor has studied to obtain an antibody which simultaneously responds to human noroviruses belonging to Genogroup GII, and has found that an antibody which binds to a particular site of the P (protruding) region of capsid protein of human norovirus GII can bind to a wide range of human noroviruses GII, whereby substantially all the human noroviruses GII of genotypes (GII/1 to GII/17) can be specifically detected.

Accordingly, the present invention is directed to the following (1) to (4):

(1) an anti-human-norovirus GII antibody that binds to at least one of epitopes which are contained in amino acid regions represented by the following formulas (1) and (2):

$$P\text{-}X^1\text{-}X^2\text{-}P\text{-}G\text{-}E \quad (1) \text{ (SEQ ID NO: 2)}$$

$$X^3\text{-}X^4\text{-}X^5\text{-}F\text{-}Y\text{-}X^6\text{-}L\text{-}X^7\text{-}P\text{-}X^8 \quad (2) \text{ (SEQ ID NO: 3)}$$

(wherein, $X^1$ represents L, V, N, T, S, M, or R; $X^2$ represents F, Y, or M; $X^3$ represents V or G; $X^4$ represents N or S; $X^5$ represents Q, P, or S; $X^6$ represents S, T, or I; $X^7$ represents A or S; and $X^8$ represents M or V), and of an epitope formed of amino acid 483 of the amino acid sequence represented by SEQ ID NO: 1, or an epitope formed of an amino acid corresponding to amino acid 483, the regions and the amino acids being present in the P domain of a capsid structural protein of a human norovirus GII.

(2) the anti-human-norovirus GII antibody according to (1) above, wherein the amino acid region represented by formula (1) is a region from amino acid 419 to amino acid 424 of the amino acid sequence represented by SEQ ID NO: 1, or a region corresponding thereto, and the amino acid region represented by formula (2) is a region from amino acid 516 to amino acid 525 of the amino acid sequence represented by SEQ ID NO: 1, or a region corresponding thereto;

(3) a human norovirus GII detection reagent containing an antibody as recited in (1) or (2) above; and (4) a method for detecting a human norovirus GII, the method comprising reacting a specimen suspected to contain the human norovirus GII with an antibody as recited in (1) or (2) above, and detecting the virus through immunological assay.

Effects of the Invention

By use of the anti-human-norovirus antibody of the present invention, the human noroviruses belonging to the group GII can be comprehensively detected, whereby a wide variety of human noroviruses of different genotypes belonging to GII can be detected comprehensively and effectively. Furthermore, since the anti-human-norovirus GII antibody of the present invention can bind to an amino acid region of the P domain, which region is thought to have less genetic mutation, the virus detection reagent using the antibody does not require antibody reconstruction so as to fit an epidemic type, which is advantageous.

BRIEF DESCRIPTION OF THE DRAWINGS

FIG. 1-1 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-2 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-3 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-4 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-5 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-6 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-7 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-8 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-9 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 1-10 An alignment chart of amino acid sequences of capsid structural proteins of human norovirus strains having 21 genotypes of GII. FIG. 1-1 to FIG. 1-10 disclose full length SEQ ID NOS 1 and 21-41, respectively, in order of appearance.

FIG. 2 A bonding state between an anti-norovirus GII monoclonal antibody (5B-18-3M) and the norovirus, obtained through X-ray crystallographic structural analysis.

MODES FOR CARRYING OUT THE INVENTION

Figure 2:
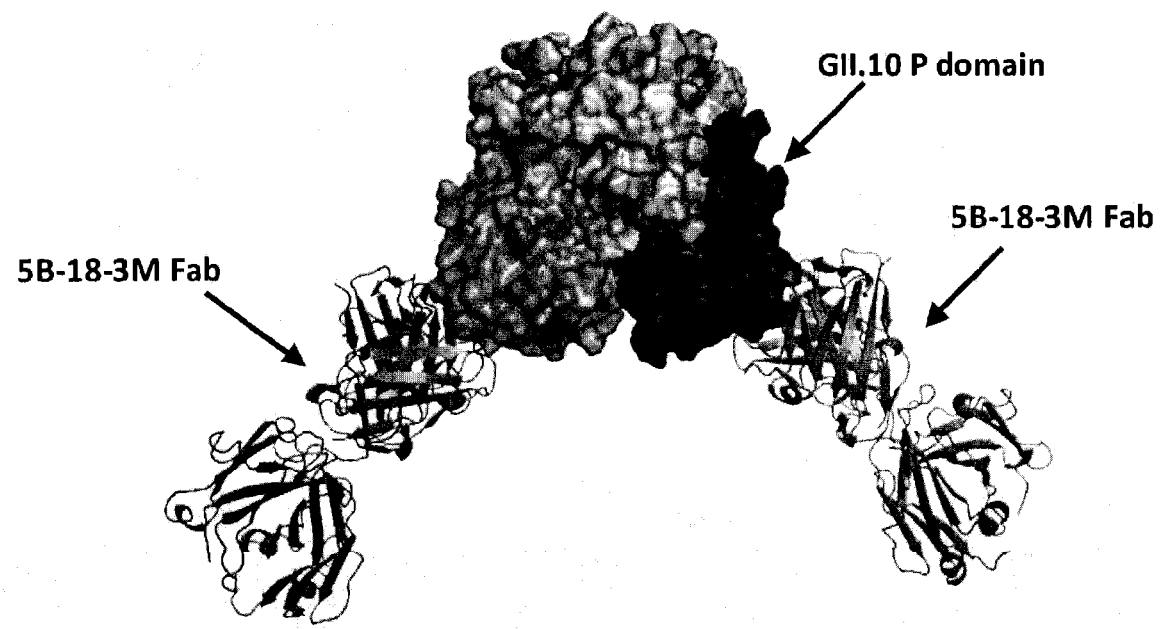

In the present specification, alphabetical letters in the formulas for the amino acid regions represent symbols of amino acids in a one-letter manner. Each sequence is given from the N-terminal to the C-terminal (from left to right).

The anti-human-norovirus GII antibody of the present invention binds to at least one of the epitopes which are contained in amino acid regions represented by the following formulas (1) and (2):

$$P\text{-}X^1\text{-}X^2\text{-}P\text{-}G\text{-}E \qquad (1)\ (\text{SEQ ID NO: 2})$$

$$X^3\text{-}X^4\text{-}X^5\text{-}F\text{-}Y\text{-}X^6\text{-}L\text{-}X^7\text{-}P\text{-}X^8 \qquad (2)\ (\text{SEQ ID NO: 3})$$

(wherein, $X^1$ represents L, V, N, T, S, M, or R; $X^2$ represents F, Y, or M; $X^3$ represents V or G; $X^4$ represents N or S; $X^5$ represents Q, P, or S; $X^6$ represents S, T, or I; $X^7$ represents A or S; and $X^8$ represents M or V), and of an epitope formed of amino acid 483 of the amino acid sequence represented by SEQ ID NO: 1, or formed of an amino acid corresponding to amino acid 483, the regions and the amino acids being present in the P domain of a capsid structural protein of a human norovirus GII.

As used herein, the term "human norovirus GII" refers to a human norovirus belonging to GII (Genogroup II).

The capsid structural protein (VP1) of the human norovirus is known to be formed of a shell domain (S domain) and a protruding domain (P domain). The S domain is thought to control assembly of VP1. According to a certain study, the following is reported. The P domain is divided into P1 and P2 subdomains, wherein the P1 subdomain interacts with the S domain, to thereby potentiate physical stability of capsid, whereas the P2 subdomain is present at the outermost shell of each virus particle. In the case of a mouse norovirus, the P2 subdomain serves as a target for a neutralizing antibody.

The amino acid regions of the present invention represented by formulas (1) and (2), and amino acid 483 of the amino acid sequence represented by SEQ ID NO: 1, or an amino acid corresponding to amino acid 483 are present in the P domain of capsid structural protein of a human norovirus GII. Therefore, conceivably, the amino acid regions and the amino acids have high sequence conservation for each genotype and have less genetic mutation. Hitherto, there has been known no antibody that recognizes such amino acid regions or amino acids.

In formula (1), P represents proline, G represents glycine, and E represents glutamic acid.

$X^1$ represents L (leucine), V (valine), N (asparagine), T (threonine), S (serine), M (methionine), or R (arginine).

$X^2$ represents F (phenylalanine), Y (tyrosine), S (serine), or M (methionine), with F being preferred.

Examples of preferred amino acid regions represented by formula (1) include the following (1-1) to (1-9):

$$P\text{-}L\text{-}F\text{-}P\text{-}G\text{-}E \qquad (1\text{-}1)\ (\text{SEQ ID NO: 4}),$$

$$P\text{-}V\text{-}F\text{-}P\text{-}G\text{-}E \qquad (1\text{-}2)\ (\text{SEQ ID NO: 5}),$$

$$P\text{-}N\text{-}F\text{-}P\text{-}G\text{-}E \qquad (1\text{-}3)\ (\text{SEQ ID NO: 6}),$$

$$P\text{-}T\text{-}F\text{-}P\text{-}G\text{-}E \qquad (1\text{-}4)\ (\text{SEQ ID NO: 7}),$$

| P-S-F-P-G-E | (1-5) (SEQ ID NO: 8), |
| P-T-Y-P-G-E | (1-6) (SEQ ID NO: 9), |
| P-M-F-P-G-E | (1-7) (SEQ ID NO: 10), |
| R-L-S-L-V-S | (1-8) (SEQ ID NO: 11), and |
| P-R-M-P-G-E | (1-9)(SEQ ID NO: 12). |

In formula (2), F represents phenylalanine, Y represents tyrosine, L represents leucine, and P represents proline.

$X^3$ represents V (valine) or G (glycine), with V being preferred.

$X^4$ represents N (asparagine) or S (serine), with N being preferred.

$X^5$ represents Q (glutamine), P (proline), or S (serine), with Q being preferred.

$X^6$ represents S (serine), T (threonine), or I (isoleucine), with S or T being preferred.

$X^7$ represents A (alanine) or S (serine), with A being preferred.

$X^8$ represents M (methionine) or V (valine), with M being preferred.

Examples of preferred amino acid regions represented by formula (2) include the following (2-1) to (2-8):

| V-N-Q-F-Y-S-L-A-P-M | (2-1)(SEQ ID NO: 13), |
| V-N-P-F-Y-T-L-A-P-M | (2-2) (SEQ ID NO: 14), |
| V-N-Q-F-Y-T-L-A-P-M | (2-3) (SEQ ID NO: 15), |
| V-N-Q-F-Y-T-L-A-P-V | (2-4) (SEQ ID NO: 16), |
| V-N-Q-F-Y-S-L-A-P-M | (2-5) (SEQ ID NO: 17), |
| G-N-Q-F-Y-T-L-A-P-M | (2-6) (SEQ ID NO: 18), |
| V-N-Q-F-Y-S-L-A-P-V | (2-7) (SEQ ID NO: 19), and |
| V-S-S-F-Y-I-L-S-P-V | (2-8)(SEQ ID NO: 20). |

The amino acid region represented by the above formula (1) or (2) is present in the P domain of capside structural protein of human norovirus GII. In the case of 485 strain of genotype GII/1, the amino acid region represented by formula (1) corresponds to an amino acid region from amino acid residue 419 to amino acid residue 424 of the amino acid sequence represented by SEQ ID NO: 1, and the amino acid region represented by formula (2) corresponds to an amino acid region from amino acid residue 516 to amino acid residue 525 of the amino acid sequence represented by SEQ ID NO: 1.

In the present invention, the amino acid region corresponding to the region from amino acid 419 to amino acid 424 of the amino acid sequence represented by SEQ ID NO: 1, the amino acid region corresponding to the region from amino acid 516 to amino acid 525 of the amino acid sequence represented by SEQ ID NO: 1, and the amino acid corresponding to amino acid 483 of the amino acid sequence represented by SEQ ID NO: 1 mean, for example, regions or amino acid corresponding to the region from amino acid 419 to amino acid 424 of the amino acid sequence represented by SEQ ID NO: 1, the region from amino acid 516 to amino acid 525 of the amino acid sequence represented by SEQ ID NO: 1, and amino acid 483 of the amino acid sequence represented by SEQ ID NO: 1, which are given through alignment with each genotype based on the amino acid sequence of the VP 1 of genotype GII/1 485 strain by means of genetic information processing software GENATYX (see FIG. 1). Through alignment of the amino acid sequence of VP1 through such a method, a specific region of the amino acid sequence in the P domain of each human norovirus GII can be determined, even when a deletion is present in the amino acid sequence. A corresponding homologous region is thought to be present in the same region in the 3-dimensional structure, indicating the possible presence of the same epitope of human norovirus GII.

In the case of NG1 strain shown in FIG. 1, the region from amino acid 419 to amino acid 424 of the amino acid sequence represented by SEQ ID NO: 1 corresponds to a region from amino acid 426 to amino acid 431; the region from amino acid 516 to amino acid 525 of the amino acid sequence represented by SEQ ID NO: 1 corresponds to a region from amino acid 523 to amino acid 532; and amino acid 483 corresponds to amino acid 490.

The anti-human-norovirus GII antibody of the present invention binds to an epitope contained in the aforementioned amino acid region or to an epitope formed of the amino acid.

As used herein, the term "epitope" refers to an antigenic determinant and, more specifically, to a structural site specifically binding to an antibody. The epitope of the present invention may be a consecutive amino acids of a part of the amino acid region or amino acids present discretely in the region.

Also, the term "binding" refers to an interaction between a ligand and a substrate, which may be differentiated from a background or a non-specific or specific interaction.

The anti-human-norovirus GII antibody of the present invention at least binds to an epitope contained in the amino acid region represented by the aforementioned formula (1) or (2), or to an epitope formed of amino acid 483 of the amino acid sequence represented by SEQ ID NO: 1, or to an epitope formed of an amino acid corresponding to amino acid 483. Preferably, the antibody of the present invention can bind to all of the epitopes.

The epitope contained in the amino acid region represented by formula (1) is preferably "$X^1$," and the epitope contained in the amino acid region represented by formula (2) is preferably "$X^4$" and/or "Y-$X^6$-L."

Thus, in the case of GII/1 genotype 485 strain, the epitope is preferably one or more selected from among L of amino acid 420 of the amino acid sequence represented by SEQ ID NO: 1 in the amino acid region represented by formula (1-1); N of amino acid 517, and Y-S-L of the region of amino acids 520 to 522, in the amino acid region represented by formula (2-1); and E of amino acid 483.

In the case of GII/1 genotype NG1 strain, the epitope is preferably one or more selected from among V of amino acid 427 of the amino acid sequence represented by SEQ ID NO: 1 in the amino acid region represented by formula (1-2); N of amino acid 524, and Y-S-L of the region of amino acids 527 to 529, in the amino acid region represented by formula (2-2); and E of amino acid 490.

As described in Table 1 hereinbelow, the anti-human-norovirus GII antibody can bind to substantially all of the following noroviruses belonging to the GII genogroup (GII/1 to GII/17): 485 strain, (GII/1), NG1 strain (GII/2), 809 strain (GII/3), 18-3 strain (GII/3), 336 strain (GII/3), 104 strain (GII/4), 754 strain (GII/5), 7k strain (GII/6), 445 strain (GII/6), 10-25 strain (GII/7), U25 strain (GII/8), 876 strain (GII/12), NG15 strain (GII/13), 47 strain (GII/14), Kamo strain (GII/15), and Alph strain (GII/17). However, the anti-human-norovirus GII antibody does not bind to a norovirus belonging to the GI genogroup.

No particular limitation is imposed on the species of the animal from which the anti-human-norovirus GII antibody of the present invention is obtained. Among such animals, rat is preferred from the viewpoint of ease in production of the antibody.

The anti-human-norovirus GII antibody of the present invention may be of any required form such as IgG, IgA, IgY, IgD, IgM, IgE, or a part of one or more of these; e.g., a heavy chain, a light chain, Fc, or F(ab).

The anti-human-norovirus GII antibody employed in the present invention may be obtained, through known means, as a polyclonal antibody or a monoclonal antibody. Monoclonal antibodies derived from a mammal include those produced by a hybridoma, and those produced by a host genetically transformed with an expression vector containing the corresponding antibody gene.

Generally, such a hybridoma producing an anti-human-norovirus antibody may be produced through a known technique in the following manner. Specifically, recombinant GII norovirus-like particles (VLPs) are used as a sensitizing antigen, and are immunized though a routine immunization method. The thus-produced immunocytes are fused with known parent cells through a conventional cell fusion method. Then, through a conventional screening method, cells producing a monoclonal antibody are selected.

The recombinant norovirus GII VLP may be produced through the following procedure. Firstly, a gene sequence of capsid of a human norovirus GII is inserted into a transfer vector. Sf9 cells are transfected simultaneously with baculovirus DNA and the aforementioned plasmid, whereby a recombinant virus is produced through homologous recombination. The recombinant virus is then proliferated, to thereby yield a seed virus. Subsequently, a protein is expressed in Tn5 cells, and a recombinant norovirus GII VLP is purified from the cells or a relevant culture supernatant through a known method.

No particular limitation is imposed on the mammal to be immunized with a sensitizing antigen, but the mammal is preferably selected in consideration of compatibility with parent cells to be used in cell fusion. Generally, rodents such as mouse, rat, and hamster are employed.

Immunization of an animal with a sensitizing antigen is carried out through a known method. In one procedure, a sensitizing antigen is intraperitoneally or subcutaneously injected to a mammal. More specifically, the sensitizing antigen is diluted and suspended with an appropriate amount of PBS (phosphate-buffered saline) or physiological saline. If needed, the suspension is mixed with an appropriate amount of a conventional adjuvant such as Freund's complete adjuvant. The thus-prepared suspension is emulsified, and the emulsion is administered subcutaneously, intradermally, or intraperitoneally to an animal for temporary stimulation. The operations are repeated in accordance with needs. The amount of antigen to be administered is appropriately determined depending on the administration route and the species of the animal. Generally, the unit dose is preferably about 10 μg to about 1 mg. After immunization and confirmation of rise in serum level of an antibody of interest, blood is collected from the mammal. Through purification of serum components, a polyclonal antibody can be produced. In purification of serum components, an affinity column to which a sensitizing antigen has been fixed or the like may be employed.

For producing a monoclonal antibody, immunocytes are removed from the antibody-level-elevated mammal and subjected to cell fusion. Among immunocytes, splenic cells are particularly preferred in cell fusion.

Myeloma cells of a mammal, which are counter parent cells to be fused with the aforementioned immunocytes, include known cell strains such as P3×63, NS-1, MPC-11, and SP2/0. Myeloma cells of these strains are appropriately used.

The cell fusion between the immunocytes and myeloma cells may be carried out in accordance with a known method, such as a method of Kohler et al. (Kohler et al., Nature, vol., 256, p. 495-497 (1975)). Specifically, immunocytes and myeloma cells are mixed together in a nutrient culture medium such as RPMI1640 culture medium or MEM culture medium, in the presence of a cell fusion promoter such as polyethylene glycol (PEG: average molecular weight: 1,000 to 6,000, concentration: 30 to 60%) or Sendai virus (HVJ) with an optional promoter aid such as dimethyl sulfoxide, to thereby form hybridomas.

The hydridomas formed through cell fusion are cultured in a selective medium such as a medium containing hypoxanthine, thymidine, and aminopterin (HAT medium) for 1 to 7 days, and separated from unfused cells. Hybridomas producing an antibody of interest are further selected. The thus-selected hybridoma(s) is(are) monoclonized through a known limiting dilution analysis method, to thereby establish a monoclonal-antibody-producing hybridoma.

The activity of the antibody produced by the hybridoma may be detected through a known method, such as ELISA, an agglutination reaction method, or radioimmunoassay.

A target monoclonal antibody may be recovered from the thus-produced hybridoma through, for example, a method including culturing the hybridoma through a routine method and collecting the culture supernatant or a method including administering the hybridoma to a mammal compatible therewith, proliferating the hybridoma, and collecting the ascites of the mammal.

The target antibody may be purified through known purification means such as salting out, gel filtration, ion-exchange chromatography, or affinity chromatography.

When the anti-human-norovirus antibody of the present invention is applied to an immunological assay method, human norovirus GII present in a specimen can be specifically detected and measured.

No particular limitation is imposed on the immunological assay method, but a sandwich method employing an anti-norovirus GII antibody and a labeled anti-norovirus GII antibody is preferred. A sandwich method employing an immobilized anti-norovirus GII antibody and a labeled anti-norovirus GII antibody is more preferably employed.

Examples of preferred immobilized anti-norovirus GII antibodies include those immobilized on an insoluble support such as a polystyrene plate, latex particles, magnetic particles, a glass fiber membrane, a nylon membrane, a nitrocellulose membrane, or an acetylcellulose membrane.

Examples of the label of the labeled anti-human-norovirus GII antibody which may be used in the invention include known labels, such as radioisotopes (e.g., $^{32}P$, $^{35}S$, and $^{3}H$), enzymes (e.g., peroxidase, alkaline phosphatase, and luciferase), proteins (e.g., avidin), low-molecular-weight compounds (e.g., biotin), fluorescent substances (e.g., FITC), chemiluminescent substances (e.g., acridinium), latex particles (e.g., colored latex particles and fluorescent latex particles), metal (e.g., noble metals (e.g., gold, silver, and platinum)) colloid particles, and carbon atoms.

Norovirus GII present in a specimen is detected on the basis of reaction between the norovirus present in the specimen and an immobilized anti-norovirus GII antibody. In the case of sandwich assay, a specimen-containing liquid is reacted with an immobilized anti-norovirus GII antibody, and then with the aforementioned labeled antibody. Alternatively, a specimen-containing liquid may be reacted simultaneously with an immobilized anti-norovirus GII antibody and the labeled antibody. After completion of reaction, the level of the label present in a complex formed of the norovirus present in the specimen, the immobilized anti-norovirus GII antibody, and the labeled antibody is measured, whereby the norovirus GII level of the specimen can be determined. The amount of the label may be measured through means depending on the type of the label. In the case where an enzyme or avidin is used as a label, a substrate is added after reaction, and the enzyme activity is measured. In the case where a fluorescent substance (including fluorescent latex particles) or a chemiluminescent substance is used as a label, signals are measured under such conditions that no quenching occurs. In the cases of colored latex particles, metal colloid particles, carbon particles, etc., signals are measured visually or by reflected light or the like.

In the present invention, norovirus GII is more preferably detected through ELISA or immunochromatography.

The detection reagent (kit) containing the anti-human-norovirus GII antibody of the present invention preferably contains an immobilized anti-human-norovirus GII antibody of the present invention, a diluent for a specimen, a labeled anti-norovirus GII antibody, a reaction substrate, and other components.

EXAMPLES

Example 1

Preparation of Anti-Norovirus GII Monoclonal Antibody

The antibody employed in the method of the present invention was produced through the following procedure.

Mice were immunized several times with GII norovirus-like particles (VLPs) (50 µg) by administering a mixture of VLPs and an adjuvant to the abdominal cavity of each mouse. A rise in serum titer was confirmed. The mice were boosted (via intravenous administration), and 3 days after the booster, the spleen was removed from each mouse, to thereby obtain splenic cells. The cells were fused with mouse myeloma cells (10:1 by no. of cells) in the presence of polyethylene glycol 3500, to thereby produce hybridoma cells. The cells were cultured for one week at 37° C. under $CO_2$, and the presence of anti-norovirus antibody in a culture supernatant was checked. Cells in a positive well where production of the antibody was observed were diluted through the limiting dilution method, and the cells were cultured for 2 weeks. Then, the presence of anti-norovirus antibody in a culture supernatant was checked again. Thereafter, cells in a positive well where production of the antibody was observed were diluted again through the limiting dilution method, and the same culturing was performed. In this stage, the cells which were able to produce an anti-norovirus antibody were cultured in a flask. A part of the culture was suspended in 10% dimethyl sulfoxide (DMSO)-containing fetal calf serum (FCS) ($5 \times 10^6$ cells/mL), and the suspension was stored in liquid nitrogen.

The reactivity of the produced antibodies in a culture supernatant of each well to norovirus was investigated. The norovirus-like particles (VLPs) were dissolved in 140 mM NaCl, 2.7 mM KCl, 10 mM $Na_2HPO_4$, and 1.8 mM $KH_2PO_4$, pH: 7.3 (hereinafter abbreviated as PBS, pH7.3). The norovirus-like particle (VLP)/PBS, pH7.3 solution was added to the wells of a plastic microtiter plate (Nunc-Immuno™ Module F8 Maxisorp™ Surface plate, product of Nalge Nunc International) at 100 µL/well. The norovirus-like particles (VLPs) were immobilized on the microtiter plate under the conditions of 0.05 µg/well, at 4° C., for 12 hours. Twelve hours after immobilization, the norovirus-like particle (VLP)/PBS, pH7.3 solution added to the wells was removed through decantation. To the wells of the microtiter plate, 145 mM NaCl, 3.6 mM $Na_2HPO_4$, 1.4 mM $KH_2PO_4$, and 0.05% (v./v.) Tween20 (hereinafter abbreviated as PBS-T) were added at 200 µL/well, and PBS-T was decanted out, to thereby wash excess norovirus-like particles (VLPs) adsorbed in the well. The washing step was performed twice in total.

Subsequently, 145 mM NaCl, 7.2 mM $Na_2HPO_4$, 2.8 mM $KH_2PO_4$, 1% (wt./v.) BSA, and 5% (wt./v.) lactose (hereinafter the solution is referred to as antigen-immobilized plate blocking solution) were added to the wells of the plate at 200 µL/well, to thereby perform blocking in the wells of norovirus-like particle (VLP)-immobilized microtiter plate at 4° C. for 12 hours. Twelve hours after blocking, the microtiter plate was maintained at 4° C. The reactivity of the antibodies in a culture supernatant was checked by use of the norovirus-like particle (VLP)-immobilized microtiter plate after completion of blocking. To the wells of the norovirus-like particle (VLP)-immobilized microtiter plate, a supernatant of a hybridoma culture was added at 100 µL/well, and the plate was heated at 37° C. for one hour. Subsequently, the culture supernatant added to the wells was removed through decantation. Then, PBS-T was added to the wells of the microtiter plate at 200 µL/well, and PBS-T was decanted out for washing. The washing step was performed thrice in total.

Subsequently, peroxidase-conjugated goat anti-mouse immunoglobulins (product of DAKO) were added to the wells at 100 µL/well (dilution factor of 2,000: 0.55 µg/mL), and the plate was heated at 37° C. for one hour. The enzyme-labeled antibodies were diluted with 145 mM NaCl, 3.6 mM $Na_2HPO_4$, 1.4 mM $KH_2PO_4$, 0.05% (v./v.) Tween 20, and 0.5% (wt./v.) BSA (hereinafter may be referred to as enzyme-labeled antibody dilution diluent). Then, the enzyme-labeled antibodies added to the wells were removed through decantation. PBS-T was added to the wells of the microtiter plate at 200 µL/well, and PBS-T was decanted out for washing. The washing step was performed thrice in total. Subsequently, 3,3',5,5'-tetramethylbenzidine (hereinafter abbreviated as TMB) solution (TMB One-Step Substrate System, product of DAKO) serving as a peroxidase enzymatic reaction substrate solution was added to the wells at 100 µL/well, and the plate was maintained at 25° C. for 30 minutes. Immediately after, 313 mM $H_2SO_4$ solution (hereinafter may be referred to as reaction-terminating solution) was added to the substrate reaction liquid in the wells at 100 µL/well, to thereby terminate enzymatic reaction in the wells.

The absorbance of each well was measured at 450 nm and 630 nm, and the difference between the measurements at 450 nm and 630 nm was employed as an index for assessing reactivity (Josephy P. D., Mason R. P., et al. (1982), J. Biol. Chem. 257, 3669-3675). Meanwhile, many have reported about colorimetric analysis using TMB, since the first such report by Bos E. S. et al. in 1981 (Bos E. S. et al. (1981), J. Immunoassay. 2, 187-204). Therefore, the technique has been established on a reliable basis.

As a result, monoclonal hybridoma cells exhibiting high reactivity of anti-norovirus antibody to the immobilized norovirus-like particles (VLPs) were selected. The class and subclass of the immunoglobulin in the culture supernatant (100 µL) were determined by means of Immunoglobulin Typing Kit, Mouse (product of Wako Pure Chemical Industries, Ltd.) in terms of each clone. On the basis of the results, only the IgG class of the thus-obtained monoclonal cell library was subjected to the ascites method, according to the following procedure.

Specifically, these cells were cultured in a 25-mL flask and then in a 75-mL flask. The cultured cells were intraperitoneally injected to pristane-treated mice, and ascites was collected therefrom.

In selection of monoclonal hybridoma cells, monoclonal hybridoma cells exhibiting high reactivity of anti-norovirus antibody to the P-domain of the immobilized norovirus-like particles (VLPs) are selected instead of monoclonal hybridoma cells exhibiting high reactivity of anti-norovirus antibody to the immobilized norovirus-like particles (VLPs), whereby a hybridoma that can produce a monoclonal antibody that can bind to an amino acid region in the P domain can be selected at high reproducibility.

In selection of monoclonal hybridoma cells, the bonding state between the monoclonal antibody and norovirus is confirmed through the same method as described in Example 3 hereinbelow, whereby a hybridoma that can produce a monoclonal antibody that can bind to an amino acid region in the P domain can be selected at high reproducibility.

In the method employed in Example 1, the P-domain protein of norovirus-like particles (VLPs) is immunized instead of GII norovirus-like particles (VLPs), whereby a hybridoma that can produce a monoclonal antibody that can bind to an amino acid region in the P domain can be obtained at high reproducibility. A method for obtaining the P-domain protein is described in Example 3.

According to the present invention, the amino acid regions represented by formulas (1) and (2) and amino acid 483 of the amino acid sequence represented by SEQ ID NO: 1 or an amino acid sequence corresponding thereto are selected, and a polypeptide formed of the amino acid sequences is produced therefrom. Through immunization with the polypeptide, a hybridoma that can produce a monoclonal antibody that can bind to an amino acid region in the P domain can be obtained at high reproducibility.

The polypeptide may be used as an antigen of human norovirus GII.

<Purification of Anti-Norovirus GII Monoclonal (IgG) Antibody>

The thus-obtained ascites (10 mL) was mixed with a turbid serum treatment agent (FRIGEN (registered trademark) II, product of Kyowa Pure Chemical Co., Ltd.) at a volume ratio of 1.5:1, and the mixture was stirred with shaking for 1 to 2 minutes, to thereby defat the ascites. The thus-treated ascites was centrifuged by means of a centrifuge at 3,000 rpm (1,930×g) for 10 minutes, to thereby recover a clear ascites centrifugation supernatant (10 mL). The ascites centrifugation supernatant (10 mL) was fractionated with ammonium sulfate (final concentration: 50%; ammonium sulfate saturation) for one hour in an ice bath, and a precipitated immunoglobulin fraction was suspended and dissolved in PBS. The ammonium sulfate fractionation was performed twice in total, to thereby recover a crude immunoglobulin fraction from the ascites. The thus-obtained crude immunoglobulin fraction (10 mL) was mixed with an equiamount of 20 mM sodium phosphate, pH: 7.0 (hereinafter referred to as 20 mM NaPB, pH7.0), and the mixture was purified through an affinity column; Protein G column (HiTrap Protein G HP, 5 mL: product of Amersham BioSciences). Specifically a sample was caused to be adsorbed onto a Protein G column, and then, 20 mM NaPB, pH7.0 (50 mL) was caused to pass through the Protein G column, to thereby remove miscellaneous matters other than IgG contained in the sample. Thereafter, IgG adsorbed on Protein G column was eluted with 0.1 M glycine-HCl, pH2.7. A fraction immediately after start of elution through the column was neutralized with 1 M tris(hydroxymethyl)aminomethane-HCl, pH9.0 (hereinafter, tris(hydroxymethyl)aminomethane is abbreviated as Tris), and the neutralized product was recovered. After neutralization, the affinity purified product was dialyzed against a 500-fold volume of PBS at 4° C. for 6 hours. The dialysis was performed twice in total. In dialysis, a cellulose tube for dialysis (product of Viskase Companies) was employed as a dialysis membrane. The thus-recovered IgG fraction was employed as an anti-norovirus GII monoclonal antibody (5B-18-3M) purified product, and the product was stored at 4° C. and used in the subsequent procedure. Notably, all the purification steps were performed by means of the aforementioned Protein G column connected to BioLogic LP system (product of Bio Rad Laboratories) at a flow rate of 1 mL/min.

Example 2

Reactivity of Anti-Norovirus GII Monoclonal Antibody

By use of the anti-norovirus GII monoclonal antibody (5B-18-3M) produced in Example 1, norovirus GII detection reagents employing an immunochromatographic method were produced through the following procedure.

Firstly, a solution containing the anti-norovirus GII monoclonal antibody (5B-18-3M) in an amount of 0.36 to 1.45 mg/mL was applied onto a nitrocellulose membrane sheet in a line pattern so as to attain a coating amount of 0.25 to 1.00 µL/5 mm, to thereby provide test lines. A control line was provided through applying an anti-mouse globulin antibody in the same manner.

A solution containing latex to which the anti-norovirus GII monoclonal antibody (5B-18-3M) was bound in an amount of 0.04 to 0.15 w/v % was employed as an antibody-bound latex solution (5B-18-3M). A conjugate pad was impregnated with the latex solution and then dried.

A sample pad, the membrane, the conjugate pad, and an absorption pad were stacked in this order on a plastic backing sheet, such that adjacent members partially overlapped, and the stacked body was coated with a plastic laminate. The product was cut to a width of 5 mm, to thereby provide test strips.

The reactivity of the above-prepared reagent to a norovirus of each genotype was checked through the following procedure.

A recombinant antigen of each genotype of norovirus was suspended in a diluent, and the thus-obtained floating antigen (75 µL) was added dropwise to a sample pad of the above-produced test strip. The test strip was allowed to stand at 15 to 30° C. for 15 minutes, and then the presence of a line was checked. Table 1 shows the results. Note that 124 strain refers to Hu/NV/GI/Aichi124-89/89/JP (GeneBank accession number: AB031013) strain; 258 strain refers to Hu/NV/GI/Funabashi258/96/JP (GeneBank accession number: AB078335) strain; 645 strain refers to Hu/NV/GI/Kashiwa645/99/JP (GeneBank accession number: BD011871) strain; CV strain refers to Hu/NV/GI/Chiba407/87/JP (GeneBank accession number: AB042808) strain; W18 strain refers to Hu/NV/GI/WUG1/00/JP (GeneBank accession number: AB081723) strain; #8 strain refers to Hu/NV/GI/8/99/JP (GeneBank accession number: AB058547) strain; 485 strain refers to Hu/NV/GII/Noda485/00/JP (GeneBank accession number: unregistered) strain; NG1 strain refers to Hu/NV/GII/NG1/

02/JP (GeneBank accession number: AB195225) strain; 809 strain refers to Hu/NV/GII/Sanbu809/98/JP (GeneBank accession number: BD011876); 18-3 strain refers to Hu/NV/GII/Matsudo18/00/JP (GeneBank accession number: unregistered) strain; 336 strain refers to Hu/NV/GII/Kashiwa336/00/JP (GeneBank accession number: unregistered) strain; 104 strain refers to Hu/NV/GII/Narita104/97/JP (GeneBank accession number: unregistered) strain; 754 strain refers to Hu/NV/GII/Ichikawa754/98/JP (GeneBank accession number: BD011877) strain; 7k strain refers to Hu/NV/GII/Ueno7k/94/JP (GeneBank accession number: AB078337) strain; 445 strain refers to Hu/NV/GII/Sanbu445/00/JP (GeneBank accession number: unregistered) strain; 10-25 strain refers to Hu/NV/GII/Osaka10-25/99/JP (GeneBank accession number: BD011881) strain; U25 strain refers to Hu/NV/GII/SaitamaU25//JP (GeneBank accession number: AB039780) strain; 1876 strain refers to Hu/NV/GII/Chitta/Aichi76-96/96/JP (GeneBank accession number: AB032758) strain; NG15 strain refers to Hu/NV/GII/NG15/03/JP (GeneBank accession number: unregistered) strain; 47 strain refers to Hu/NV/GII/Kashiwa47/97/JP (GeneBank accession number: AB078334) strain; Kamo strain refers to Hu/NV/GII/Kamo8/03/JP (GeneBank accession number: unregistered) strain; and Alph strain refers to Hu/NV/GII/Alph23//JP (GeneBank accession number: unregistered) strain.

TABLE 1

| Genogroup | Genotype | Virus strain | Reactivity |
|---|---|---|---|
| Genogroup I | GI/1 | 124 | − |
| | GI/2 | 258 | − |
| | GI/3 | 645 | − |
| | GI/4 | CV | − |
| | GI/6 | W18 | − |
| | GI/11 | #8 | − |
| Genogroup II | GII/1 | 485 | + |
| | GII/2 | NG1 | + |
| | GII/3 | 809 | + |
| | GII/3 | 18-3 | + |
| | GII/3 | 336 | + |
| | GII/4 | 104 | + |
| | GII/5 | 754 | + |
| | GII/6 | 7k | + |
| | GII/6 | 445 | + |
| | GII/7 | 10-25 | + |
| | GII/8 | U25 | + |
| | GII/12 | 1876 | + |
| | GII/13 | NG15 | + |
| | GII/14 | 47 | + |
| | GII/15 | Kamo | + |
| | GII/17 | Alph | + |

As is clear from Table 1, the anti-norovirus GII monoclonal antibody (5B-18-3M) was able to bind to virtually all the noroviruses belonging to the GII genegroup divided into GII/1 to GII/17, including 485 strain (GII/1), NG1 strain (GII/2), 809 strain (GII/3), 18-3 strain (GII/3), 336 strain (GII/3), 104 strain (GII/4), 754 strain (GII/5), 7k strain (GII/6), 445 strain (GII/6), 10-25 strain (GII/7), U25 strain (GII/8), 876 strain (GII/12), NG15 strain (GII/13), 47 strain (GII/14), Kamo strain (GII/15), and Alph strain (GII/17), and did not bind to noroviruses belonging to the GI genegroup.

Example 3

X-Ray Crystallographic Structural Analysis

In order to elucidate the bonding state between the anti-norovirus GII monoclonal antibody (5B-18-3M) and norovirus, the following X-ray crystallographic structural analysis was carried out.
(1) Preparation of Samples
<Protein Expression of Norovirus P Domain, and Purification and Crystallization of Protein>
P domain (amino acid residues 224 to 538) (amino acid length: 314), which is similar to the full length of the P domain of norovirus Vietnam 026 GII.10, was designed for protein expression in E. coli. The designed P domain was inserted into a pMal-c2x vector obtained by cutting with restriction enzymes BamHI and NotI (product of New England Biolabs), to thereby produce a clone for protein expression. The clone was transformed to E. coli BL21 cells (product of Invitrogen), and protein expression was induced with IPTG (1 mM) at 22° C. for 18 hours. The thus-obtained His-tagged fusion P domain protein was purified with a Ni column (product of Qiagen) and treated overnight with HRV-3C protease (product of Novagen) at 4° C. Thereafter, the thus-treated liquid was caused to pass through the Ni column, to thereby purify the P domain.
The P domain was further purified through molecular sieve chromatography by use of Superdex 200 column (GE) and concentrated to 2 to 10 mg/mL. Before crystallization, the purified P domain was stored in GFB (0.35 M NaCl, 2.5 mM Tris, pH 7.0, 0.02% $NaN_3$).
<Preparation of Fab Fragments of Anti-Norovirus GII Monoclonal Antibody (5B-18-3M)>
Fab fragments were prepared by use of the purified 5B-18-3M IgG (about 60 mg). Specifically, 5B-18-3M IgG was reduced with 100 mM dTT at 37° C. for one hour. The thus-reduced 5B-18-3M IgG was dialyzed in a dialysis cassette at 4° C. for one hour. Then, the buffer was changed to GFB containing 20 mM HEPES (pH: 7.7), and alkylation was performed with GFB containing 2 mM iodoacetamide at 4° C. for 48 hours. Subsequently, the cassette was transferred to new GFB containing no iodoacetamide, and the buffer was substituted at 4° C. for one hour. 5B-18-3M IgG was concentrated to 5 mg/mL, and digested with papain by means of a kit (pierce, Rockford, USA). The digested 5B-18-3M IgG was purified with Protein A column in terms of Fab. The Fab was further purified through molecular sieve chromatography by use of Superdex 200 column (GE) and concentrated to 5 mg/mL. The Fab was stored in GFB.
The thus-purified P domain of norovirus GII.10 and 5B-18-3M Fab were mixed together at 1:1, and the mixture was allowed to react at 25° C. for one hour. Finally, the reaction product was purified through molecular sieve chromatography.
<Co-Crystallization of a Complex of Norovirus P Domain and Fab of Anti-Norovirus GII Monoclonal Antibody (5B-18-3M)>
The aforementioned complex of the P domain of norovirus and Fab of the anti-norovirus GII monoclonal antibody (5B-18-3M) was crystallized under conditions slightly different from those employed in the hanging-drop vapor diffusion method using a reagent of Hampton Research Corp.
For the purpose of the research, a GII.10 P domain-Fab complex was mixed with GFB containing PEG 400 (40% v/v), PEG 3350 (5% w/v), and 0.1 M acetic acid (pH: 5.5) at a ratio of 1:1, to thereby grow crystals of a P-domain-Fab complex. Before data collection, the crystals were transferred to an anti-freezing agent; i.e., a mixture of 30% ethylene glycol containing GFB.

(2) Structural Analysis

X-ray diffraction data of the crystalline complex of the anti-norovirus GII monoclonal antibody (5B-18-3M) and the P domain of norovirus GII.10 capsid protein were created by use of beam lines of Argonne National Laboratory (Argonne, Ill.): Southeast Regional Collaborative Access Team (SER-CAT) 22-ID and 22-BM. The diffraction data were processed by protein-low molecule data processing software HKL2000 with a program package XDS. In structural analysis, PDB (Protein Data Bank) code 1WEJ was used as a search model for Fab of the anti-norovirus GII monoclonal antibody, and PDB code 2OBR was used as a search model for the P domain of norovirus capsid. The stearic structure was constructed by use of molecular substitution-based structural analysis software PHASER, from the diffraction data and the amino acid sequences of the anti-norovirus GII monoclonal antibody (5B-18-3M) and the P domain of norovirus GII.10 capsid protein.

Thereafter, the stearic structure was refined with a manual model provided in model building software COOT and modified with a refining program REFMAC, TLS refinement, and automatic structure determination software PHENIX. By means of CCP4, superposition and root mean square deviation (RMSD) were calculated. Thus, the stearic structure was drawn by molecular graphic tool PyMOL.

(3) Results

Through the above procedure, the structure shown in FIG. 2 was obtained. Based on the thus-obtained structure, amino acid sequences of the P domain of norovirus GII.10 capsid protein in the site where the anti-norovirus GII monoclonal antibody (5B-18-3M) was bound to the P domain of GII.10 capsid protein were identified. As a result, three regions were found. Subsequently, homology in amino acid sequence was compared among respective noroviruses of different genotypes. As shown in FIG. 1, these three regions were highly conserved among the different genotypes.

---

The invention claimed is:

1. An anti-human-norovirus GII antibody that binds to epitopes in an amino acid region represented by (i), (ii), and (iii):
   (i) an epitope in an amino acid region of at least one amino acid sequence of formula (1):

P-X$^1$-X$^2$-P-G-E  (1) (SEQ ID NO: 2)

wherein
   X$^1$ represents L, V, N, T, S, M, or R;
   X$^2$ represents F, Y, S or M;
   (ii) an epitope in an amino acid region of at least one amino acid sequence of formula (2)

X$^3$-X$^4$-X$^5$-F-Y-X$^6$-L-X$^7$-P-X$^8$  (2) (SEQ ID NO: 3)

wherein
   X$^3$ represents V or G;
   X$^4$ represents N or S;
   X$^5$ represents Q, P, or S;
   X$^6$ represents S, T, or I;
   X$^7$ represents A or S; and
   X$^8$ represents M or V; and
   (iii) an epitope in an amino acid region comprising amino acid 483 of the amino acid sequence represented by SEQ ID NO: 1, or comprising an amino acid corresponding to amino acid 483 of the amino acid sequence represented by SEQ ID NO: 1,
   wherein the amino acid region represented by (i), (ii), and (iii) is present in a P domain of a capsid structural protein of a human norovirus GII.

2. The anti-human-norovirus GII antibody according to claim 1, wherein the amino acid region represented by formula (1) is a region from amino acid 419 to amino acid 424 of the amino acid sequence represented by SEQ ID NO: 1, and the amino acid region represented by formula (2) is a region from amino acid 516 to amino acid 525 of the amino acid sequence represented by SEQ ID NO: 1.

3. A human norovirus GII detection reagent comprising the antibody of claim 1.

4. A method for detecting a human norovirus GII, the method comprising reacting a specimen suspected to contain the human norovirus GII with the antibody of claim 1, and performing an immunological assay to detect the virus.

5. A human norovirus GII detection reagent comprising the antibody of claim 2.

6. A method for detecting a human norovirus GII, the method comprising reacting a specimen suspected to contain the human norovirus GII with the antibody of claim 2, and performing an immunological assay to detect the virus.

7. The anti-human-norovirus GII antibody of claim 1, wherein the amino acid region represented by formula (1) is a region from amino acid 419 to amino acid 424 of the amino acid sequence represented by SEQ ID NO: 1.

8. The anti-human-norovirus GII antibody of claim 1, wherein the amino acid region represented by formula (2) is a region from amino acid 516 to amino acid 525 of the amino acid sequence represented by SEQ ID NO: 1.

9. The anti-human-norovirus GII antibody according to claim 1, wherein X$^2$ in the amino acid sequence of formula (1) is F.

10. The anti-human-norovirus GII antibody according to claim 1, wherein the amino acid sequence of formula (1) is selected from the group consisting of:

| | |
|---|---|
| P-L-F-P-G-E | (1-1)(SEQ ID NO: 4), |
| P-V-F-P-G-E | (1-2) (SEQ ID NO: 5), |
| P-N-F-P-G-E | (1-3) (SEQ ID NO: 6), |
| P-T-F-P-G-E | (1-4) (SEQ ID NO: 7), |
| P-S-F-P-G-E | (1-5)(SEQ ID NO: 8), |
| P-T-Y-P-G-E | (1-6) (SEQ ID NO: 9), |
| P-M-F-P-G-E | (1-7) (SEQ ID NO: 10), |
| P-R-M-P-G-E | (1-9) (SEQ ID NO: 12). |

11. The anti-human-norovirus GII antibody according to claim 1, wherein X$^3$ in the amino acid sequence of formula (2) is V.

12. The anti-human-norovirus GII antibody according to claim 1, wherein X$^4$ in the amino acid sequence of formula (2) is N.

13. The anti-human-norovirus GII antibody according to claim 1, wherein X$^5$ in the amino acid sequence of formula (2) is Q.

14. The anti-human-norovirus GII antibody according to claim 1, wherein X$^6$ in the amino acid sequence of formula (2) is S or T.

15. The anti-human-norovirus GII antibody according to claim 1, wherein X$^7$ in the amino acid sequence of formula (2) is A.

16. The anti-human-norovirus GII antibody according to claim 1, wherein X$^8$ in the amino acid sequence of formula (2) is M.

17. The anti-human-norovirus GII antibody according to claim 1, wherein the amino acid sequence of formula (2) is selected from the group consisting of:

| | |
|---|---|
| V-N-Q-F-Y-S-L-A-P-M | (2-1)(SEQ ID NO: 13), |
| V-N-P-F-Y-T-L-A-P-M | (2-2) (SEQ ID NO: 14), |
| V-N-Q-F-Y-T-L-A-P-M | (2-3) (SEQ ID NO: 15), |
| V-N-Q-F-Y-T-L-A-P-V | (2-4) (SEQ ID NO: 16), |
| V-N-Q-F-Y-S-L-A-P-M | (2-5) (SEQ ID NO: 17), |
| G-N-Q-F-Y-T-L-A-P-M | (2-6) (SEQ ID NO: 18), |
| V-N-Q-F-Y-S-L-A-P-V | (2-7) (SEQ ID NO: 19), and |
| V-S-S-F-Y-I-L-S-P-V | (2-8) (SEQ ID NO: 20). |

* * * * *

UNITED STATES PATENT AND TRADEMARK OFFICE
CERTIFICATE OF CORRECTION

PATENT NO.        : 9,244,072 B2                                                                Page 1 of 1
APPLICATION NO.   : 14/344784
DATED             : January 26, 2016
INVENTOR(S)       : Motohiro Miki It is certified that error appears in the above-identified patent and that said Letters Patent is hereby corrected as shown below:

On the title page, Item (86), the PCT information is incorrect. Item (86) should read:

--(86) PCT No.: PCT/JP2012/073511

§ 371 (c)(1),
    (2), (4) Date: Mar. 27, 2014--

Signed and Sealed this
Seventeenth Day of May, 2016

Michelle K. Lee
*Director of the United States Patent and Trademark Office*

SEQUENCE LISTING

```
<160> NUMBER OF SEQ ID NOS: 41

<210> SEQ ID NO 1
<211> LENGTH: 535
<212> TYPE: PRT
<213> ORGANISM: Human norovirus
<220> FEATURE:
<223> OTHER INFORMATION: 485 strain (G2/1)

<400> SEQUENCE: 1

Met Lys Met Ala Ser Asn Asp Ala Ala Pro Ser Asn Asp Gly Ala Ala
1               5                   10                  15

Gly Leu Val Pro Glu Val Asn Asn Glu Met Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro Arg Phe
        115                 120                 125

Pro Ile Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Glu Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
```

```
Lys Pro Phe Thr Leu Pro Ile Leu Thr Ile Gly Glu Leu Ser Asn Ser
225                 230                 235                 240

Arg Phe Pro Ala Pro Ile Asp Glu Leu Tyr Thr Ser Pro Asn Glu Gly
            245                 250                 255

Leu Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ser Leu Arg Gly
        275                 280                 285

Arg Ile Asn Ala His Leu Pro Asp Asn Gln His Arg Trp Asn Met Gln
290                 295                 300

Val Thr Asn Ala Asn Gly Thr Pro Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Ile Leu
                340                 345                 350

Ala Thr Trp Ser Pro Lys Phe Thr Pro Lys Leu Gly Ser Val Val Leu
            355                 360                 365

Gly Thr Trp Glu Asp Arg Asp Phe Asp Ile Asn Gln Pro Thr Arg Phe
        370                 375                 380

Thr Pro Val Gly Leu Tyr Asp Thr Asp His Phe Asn Gln Trp Ala Leu
385                 390                 395                 400

Pro Asn Tyr Ser Gly Ala Leu Thr Leu Asn Met Asn Leu Ala Pro Ser
                405                 410                 415

Val Ala Pro Leu Phe Pro Gly Glu Gln Leu Leu Phe Arg Ser His
                420                 425                 430

Ile Pro Leu Lys Gly Gly Thr Ser Asn Gly Ala Ile Asp Cys Leu Leu
            435                 440                 445

Pro Gln Glu Trp Val Gln His Phe Tyr Gln Glu Ser Ala Pro Ser Ser
        450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
                500                 505                 510

Asp Ser Trp Val Asn Gln Phe Tyr Ser Leu Ala Pro Met Gly Thr Gly
            515                 520                 525

Asn Gly Arg Arg Arg Val Gln
530                 535

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Val, Asn, Thr, Ser, Met or Arg
<220> FEATURE:
<221> NAME/KEY: MOD_RES
<222> LOCATION: (3)..(3)
<223> OTHER INFORMATION: Phe, Tyr or Met
```

```
<400> SEQUENCE: 2

Pro Xaa Xaa Pro Gly Glu
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Gly
<220> FEATURE:
<221> NAME/KEY: MOD_RES
<222> LOCATION: (2)..(2)
<223> OTHER INFORMATION: Asn or Ser
<220> FEATURE:
<221> NAME/KEY: MOD_RES
<222> LOCATION: (3)..(3)
<223> OTHER INFORMATION: Gln, Pro or Ser
<220> FEATURE:
<221> NAME/KEY: MOD_RES
<222> LOCATION: (6)..(6)
<223> OTHER INFORMATION: Ser, Thr or Ile
<220> FEATURE:
<221> NAME/KEY: MOD_RES
<222> LOCATION: (8)..(8)
<223> OTHER INFORMATION: Ala or Ser
<220> FEATURE:
<221> NAME/KEY: MOD_RES
<222> LOCATION: (10)..(10)
<223> OTHER INFORMATION: Met or Val

<400> SEQUENCE: 3

Xaa Xaa Xaa Phe Tyr Xaa Leu Xaa Pro Xaa
1               5                   10

<210> SEQ ID NO 4
<211> LENGTH: 6
<212> TYPE: PRT
<213> ORGANISM: Human norovirus

<400> SEQUENCE: 4

Pro Leu Phe Pro Gly Glu
1               5

<210> SEQ ID NO 5
<211> LENGTH: 6
<212> TYPE: PRT
<213> ORGANISM: Human norovirus

<400> SEQUENCE: 5

Pro Val Phe Pro Gly Glu
1               5

<210> SEQ ID NO 6
<211> LENGTH: 6
<212> TYPE: PRT
<213> ORGANISM: Human norovirus

<400> SEQUENCE: 6

Pro Asn Phe Pro Gly Glu
1               5

<210> SEQ ID NO 7
<211> LENGTH: 6
```

```
<212> TYPE: PRT
<213> ORGANISM: Human norovirus

<400> SEQUENCE: 7

Pro Thr Phe Pro Gly Glu
1               5

<210> SEQ ID NO 8
<211> LENGTH: 6
<212> TYPE: PRT
<213> ORGANISM: Human norovirus

<400> SEQUENCE: 8

Pro Ser Phe Pro Gly Glu
1               5

<210> SEQ ID NO 9
<211> LENGTH: 6
<212> TYPE: PRT
<213> ORGANISM: Human norovirus

<400> SEQUENCE: 9

Pro Thr Tyr Pro Gly Glu
1               5

<210> SEQ ID NO 10
<211> LENGTH: 6
<212> TYPE: PRT
<213> ORGANISM: Human norovirus

<400> SEQUENCE: 10

Pro Met Phe Pro Gly Glu
1               5

<210> SEQ ID NO 11
<211> LENGTH: 6
<212> TYPE: PRT
<213> ORGANISM: Human norovirus

<400> SEQUENCE: 11

Arg Leu Ser Leu Val Ser
1               5

<210> SEQ ID NO 12
<211> LENGTH: 6
<212> TYPE: PRT
<213> ORGANISM: Human norovirus

<400> SEQUENCE: 12

Pro Arg Met Pro Gly Glu
1               5

<210> SEQ ID NO 13
<211> LENGTH: 10
<212> TYPE: PRT
<213> ORGANISM: Human norovirus

<400> SEQUENCE: 13

Val Asn Gln Phe Tyr Ser Leu Ala Pro Met
1               5                   10

<210> SEQ ID NO 14
<211> LENGTH: 10
<212> TYPE: PRT
<213> ORGANISM: Human norovirus
```

<400> SEQUENCE: 14

Val Asn Pro Phe Tyr Thr Leu Ala Pro Met
1               5                   10

<210> SEQ ID NO 15
<211> LENGTH: 10
<212> TYPE: PRT
<213> ORGANISM: Human norovirus

<400> SEQUENCE: 15

Val Asn Gln Phe Tyr Thr Leu Ala Pro Met
1               5                   10

<210> SEQ ID NO 16
<211> LENGTH: 10
<212> TYPE: PRT
<213> ORGANISM: Human norovirus

<400> SEQUENCE: 16

Val Asn Gln Phe Tyr Thr Leu Ala Pro Val
1               5                   10

<210> SEQ ID NO 17
<211> LENGTH: 10
<212> TYPE: PRT
<213> ORGANISM: Human norovirus

<400> SEQUENCE: 17

Val Asn Gln Phe Tyr Ser Leu Ala Pro Met
1               5                   10

<210> SEQ ID NO 18
<211> LENGTH: 10
<212> TYPE: PRT
<213> ORGANISM: Human norovirus

<400> SEQUENCE: 18

Gly Asn Gln Phe Tyr Thr Leu Ala Pro Met
1               5                   10

<210> SEQ ID NO 19
<211> LENGTH: 10
<212> TYPE: PRT
<213> ORGANISM: Human norovirus

<400> SEQUENCE: 19

Val Asn Gln Phe Tyr Ser Leu Ala Pro Val
1               5                   10

<210> SEQ ID NO 20
<211> LENGTH: 10
<212> TYPE: PRT
<213> ORGANISM: Human norovirus

<400> SEQUENCE: 20

Val Ser Ser Phe Tyr Ile Leu Ser Pro Val
1               5                   10

<210> SEQ ID NO 21
<211> LENGTH: 542
<212> TYPE: PRT
<213> ORGANISM: Human norovirus
<220> FEATURE:
<223> OTHER INFORMATION: NG1 strain (G2/2)

<400> SEQUENCE: 21

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
                20                  25                  30

Ala Gly Ala Ala Leu Ala Ala Pro Val Thr Gly Gln Thr Asn Ile Ile
            35                  40                  45

Asp Pro Trp Ile Arg Ala Asn Phe Val Gln Ala Pro Asn Gly Glu Phe
        50                  55                  60

Thr Val Ser Pro Arg Asn Ala Pro Gly Glu Val Leu Leu Ser Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
                100                 105                 110

Ala Phe Thr Ala Gly Lys Leu Val Phe Ala Ala Val Pro Pro His Phe
            115                 120                 125

Pro Val Glu Asn Leu Ser Pro Gln Gln Ile Thr Met Phe Pro His Val
        130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
                180                 185                 190

Asp Asp Val Phe Thr Val Ser Cys Arg Val Leu Thr Arg Pro Ser Pro
            195                 200                 205

Asp Phe Asp Phe Thr Tyr Leu Val Pro Pro Thr Val Glu Ser Lys Thr
        210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
                260                 265                 270

Gln Gly Thr Thr Gln Leu Gln Val Ser Gly Ile Cys Ala Phe Lys Gly
            275                 280                 285

Glu Val Thr Ala His Leu His Asp Asn Asp His Leu Tyr Asn Val Thr
        290                 295                 300

Ile Thr Asn Leu Asn Gly Pro Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys Gln Asn Ala Ala Gly His Ser Glu Pro Ala Asn
                340                 345                 350

Arg Gly His Asp Ala Val Pro Thr Tyr Thr Ala Gln Tyr Thr Pro
            355                 360                 365

Lys Leu Gly Gln Val Gln Ile Gly Thr Trp Gln Thr Asp Asp Leu Gln
        370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu

```
                    405                 410                 415
Asn Thr Asn Leu Ala Pro Ser Val Ala Pro Val Phe Pro Gly Glu Arg
        420                 425                 430

Leu Leu Phe Phe Arg Ser Tyr Ile Pro Leu Lys Gly Gly Tyr Gly Asn
        435                 440                 445

Pro Ala Ile Asp Cys Leu Leu Pro Gln Glu Trp Val Gln His Phe Tyr
        450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
            485                 490                 495

Gly Phe Val Thr Val Ser Ser Asn Thr Ser Ala Pro Val Val Val Pro
                500                 505                 510

Ala Asn Gly Tyr Phe Arg Phe Asp Ser Trp Val Asn Gln Phe Tyr Ser
            515                 520                 525

Leu Ala Pro Met Gly Ala Gly Asn Gly Arg Arg Arg Val Gln
        530                 535                 540
```

<210> SEQ ID NO 22
<211> LENGTH: 542
<212> TYPE: PRT
<213> ORGANISM: Human norovirus
<220> FEATURE:
<223> OTHER INFORMATION: MK04 strain (G2/2)

<400> SEQUENCE: 22

```
Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe His His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
```

```
            225                 230                 235                 240
        Arg Phe Pro Val Ser Ile Asp Gln Met Tyr Thr Ser Pro Asn Glu Val
                        245                 250                 255

Ile Ser Val Gln Cys Gln Asn Gly Arg Cys Thr Leu Asp Gly Glu Leu
                        260                 265                 270

Gln Gly Thr Thr Gln Leu Gln Val Ser Gly Ile Cys Ala Phe Lys Gly
                        275                 280                 285

Glu Val Thr Ala His Leu His Asp Asn Asp His Leu Tyr Asn Val Thr
                        290                 295                 300

Ile Thr Asn Leu Asn Gly Ser Pro Phe Asp Arg Ser Glu Asp Ile Pro
        305                 310                 315                 320

Ala Pro Leu Gly Val Pro Asp Phe Gln Gly Arg Val Phe Gly Val Ile
                        325                 330                 335

Ser Gln Arg Asp Lys His Asn Ser Pro Gly His Asn Glu Pro Ala Asn
                        340                 345                 350

Arg Gly His Asp Ala Val Val Pro Thr Tyr Thr Ser Gln Tyr Thr Pro
                        355                 360                 365

Lys Leu Gly Gln Ile Gln Ile Gly Thr Trp Gln Thr Asp Asp Leu Thr
                        370                 375                 380

Val Asn Gln Pro Val Lys Phe Thr Pro Val Gly Leu Asn Asp Thr Glu
        385                 390                 395                 400

His Phe Asn Gln Trp Val Val Pro Arg Tyr Ala Gly Ala Leu Asn Leu
                        405                 410                 415

Asn Thr Asn Leu Ala Pro Ser Val Ala Pro Val Phe Pro Gly Glu Arg
                        420                 425                 430

Leu Leu Phe Phe Arg Ser Tyr Ile Pro Leu Lys Gly Gly Tyr Gly Asn
                        435                 440                 445

Pro Ala Ile Asp Cys Leu Leu Pro Gln Glu Trp Val Gln His Phe Tyr
                        450                 455                 460

Gln Glu Ala Ala Pro Ser Met Ser Glu Val Ala Leu Val Arg Tyr Ile
        465                 470                 475                 480

Asn Pro Asp Thr Gly Arg Ala Leu Phe Glu Ala Lys Leu His Arg Ala
                        485                 490                 495

Gly Phe Met Thr Val Ser Ser Asn Thr Ser Ala Pro Val Val Val Pro
                        500                 505                 510

Ala Asn Gly Tyr Phe Arg Phe Asp Ser Trp Val Asn Gln Phe Tyr Ser
                        515                 520                 525

Leu Ala Pro Met Gly Thr Gly Asn Gly Arg Arg Arg Val Gln
        530                 535                 540

<210> SEQ ID NO 23
<211> LENGTH: 548
<212> TYPE: PRT
<213> ORGANISM: Human norovirus
<220> FEATURE:
<223> OTHER INFORMATION: 336 strain (G2/3)

<400> SEQUENCE: 23

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
                20                  25                  30

Ala Gly Ala Ala Ile Ala Ala Pro Leu Thr Gly Gln Gln Asn Ile Ile
                35                  40                  45

Asp Pro Trp Ile Met Asn Asn Phe Val Gln Ala Pro Gly Gly Glu Phe
```

```
            50                  55                  60
Thr Val Ser Pro Arg Asn Ser Pro Gly Glu Val Leu Leu Asn Leu Glu
 65                  70                  75                  80

Leu Gly Pro Glu Ile Asn Pro Tyr Leu Ala His Leu Ala Arg Met Tyr
                 85                  90                  95

Asn Gly Tyr Ala Gly Gly Phe Glu Val Gln Val Leu Ala Gly Asn
                100                 105                 110

Ala Phe Thr Ala Gly Lys Val Ile Phe Ala Ala Ile Pro Pro Asn Phe
                115                 120                 125

Pro Ile Asp Asn Leu Ser Ala Ala Gln Ile Thr Met Cys Pro His Val
            130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
                180                 185                 190

Asp Asp Val Phe Thr Val Ser Cys Arg Val Leu Thr Arg Pro Ser Pro
            195                 200                 205

Asp Phe Ser Phe Asn Phe Leu Val Pro Pro Thr Val Glu Ser Lys Thr
210                 215                 220

Lys Pro Phe Thr Leu Pro Ile Leu Thr Ile Ser Glu Met Ser Asn Ser
225                 230                 235                 240

Arg Phe Phe Val Pro Ile Asp Ser Leu His Thr Ser Pro Thr Glu Ser
                245                 250                 255

Val Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
            275                 280                 285

Thr Leu Thr Arg Pro Thr Asn Arg Ala Ser Asp Gln Ala Asp Thr Ala
290                 295                 300

Thr Pro Arg Leu Phe Asn His Gln Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asp
            340                 345                 350

Pro Asp Gly Thr Thr Arg Ala His Glu Ala Lys Val Asp Thr Thr Ser
            355                 360                 365

Gly Arg Phe Thr Pro Lys Leu Gly Ser Leu Glu Ile Thr Thr Glu Ser
            370                 375                 380

Asp Asp Phe Asn Gln Asn Lys Pro Thr Arg Phe Thr Pro Val Gly Ile
385                 390                 395                 400

Gly Val Asp Asn Glu Ala Asp Phe Gln Gln Trp Ile Leu Pro Asp Tyr
                405                 410                 415

Ser Gly Gln Phe Thr His Asn Met Asn Leu Ala Pro Ala Val Ala Pro
                420                 425                 430

Asn Phe Pro Gly Glu Gln Leu Leu Phe Phe Arg Ser Gln Leu Pro Ser
            435                 440                 445

Ser Gly Gly Arg Ser Asn Gly Ile Leu Asp Cys Leu Val Pro Gln Glu
            450                 455                 460

Trp Val Gln His Phe Tyr Gln Glu Ser Ala Pro Ala Gln Thr Gln Val
465                 470                 475                 480
```

```
Ala Leu Val Arg Tyr Val Asn Pro Asp Thr Gly Arg Val Leu Phe Glu
            485                 490                 495

Ala Lys Leu His Lys Met Gly Phe Met Thr Ile Ala Lys Asn Gly Asp
            500                 505                 510

Ser Pro Ile Thr Val Pro Pro Asn Gly Tyr Phe Arg Phe Glu Ser Trp
            515                 520                 525

Val Asn Pro Phe Tyr Thr Leu Ala Pro Met Gly Thr Gly Lys Gly Arg
            530                 535                 540

Arg Arg Ile Gln
545

<210> SEQ ID NO 24
<211> LENGTH: 548
<212> TYPE: PRT
<213> ORGANISM: Human norovirus
<220> FEATURE:
<223> OTHER INFORMATION: 18-3 strain (G2/3)

<400> SEQUENCE: 24

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Glu Pro Val
            20                  25                  30

Ala Gly Ala Ala Ile Ala Ala Pro Leu Thr Gly Gln Gln Asn Ile Ile
            35                  40                  45

Asp Pro Trp Ile Met Asn Asn Phe Val Gln Ala Pro Gly Gly Glu Phe
        50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Val Ile Phe Ala Ala Ile Pro Pro Asn Phe
            115                 120                 125

Pro Ile Asp Asn Leu Ser Ala Ala Gln Ile Thr Met Cys Pro His Val
        130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
            195                 200                 205

Asp Phe Ser Phe Asn Phe Leu Val Pro Pro Thr Val Glu Ser Lys Thr
        210                 215                 220

Lys Leu Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
            275                 280                 285
```

```
Thr Leu Thr Arg Pro Thr Ser Arg Ala Ser Asp Gln Ala Asp Thr Pro
    290                 295                 300

Thr Pro Arg Leu Phe Asn His Arg Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ser
        355                 360                 365

Gly Arg Phe Thr Pro Lys Leu Gly Ser Leu Glu Ile Thr Thr Glu Ser
    370                 375                 380

Asp Asp Phe Asp Thr Asn Gln Ser Thr Lys Phe Thr Pro Val Gly Ile
385                 390                 395                 400

Gly Val Asp Asn Glu Ala Glu Phe Gln Gln Trp Ser Leu Pro Asn Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Val Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Lys Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545

<210> SEQ ID NO 25
<211> LENGTH: 549
<212> TYPE: PRT
<213> ORGANISM: Human norovirus
<220> FEATURE:
<223> OTHER INFORMATION: 809 strain

<400> SEQUENCE: 25

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95
```

```
Asn Gly Tyr Ala Gly Gly Phe Glu Val Gln Val Leu Ala Gly Asn
                100                 105                 110

Ala Phe Thr Ala Gly Lys Ile Ile Phe Ala Ala Ile Pro Pro Asn Phe
            115                 120                 125

Pro Ile Asp Asn Leu Ser Ala Ala Gln Ile Thr Met Cys Pro His Val
130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
210                 215                 220

Lys Pro Phe Thr Leu Pro Ile Leu Thr Ile Ser Glu Met Ser Asn Ser
225                 230                 235                 240

Arg Phe Pro Val Pro Ile Glu Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

Val Leu Thr Arg Ser Thr Ser Arg Ala Ser Asp Gln Ala Asp Thr Ala
        290                 295                 300

Thr Pro Arg Leu Phe Asn Tyr Tyr Trp His Val Gln Leu Asp Asn Leu
305                 310                 315                 320

Asn Gly Thr Pro Tyr Asp Pro Ala Glu Asp Ile Pro Gly Pro Leu Gly
                325                 330                 335

Thr Pro Asp Pro Arg Gly Lys Val Phe Gly Val Ala Ser Gln Arg Asn
            340                 345                 350

Leu Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Asp Ser
        370                 375                 380

Asp Asp Phe Asp Gln Asn Gln Pro Thr Lys Phe Thr Pro Val Gly Ile
385                 390                 395                 400

Gly Val Asp Asn Glu Ala Glu Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Val Leu Asp Cys Leu Val Pro Gln Glu
        450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Lys Val Leu Phe Glu
                485                 490                 495

Ala Lys Leu His Lys Leu Gly Phe Met Thr Ile Ala Asn Asn Gly Asp
            500                 505                 510
```

```
Ser Pro Ile Thr Val Pro Pro Ile Asn Gly Tyr Phe Arg Phe Glu Ser
            515                 520                 525

Trp Val Asn Pro Phe Tyr Thr Leu Ala Pro Met Gly Thr Gly Asn Gly
            530                 535                 540

Arg Arg Arg Ile Gln
545

<210> SEQ ID NO 26
<211> LENGTH: 539
<212> TYPE: PRT
<213> ORGANISM: Human norovirus
<220> FEATURE:
<223> OTHER INFORMATION: 104 strain (G2/4)

<400> SEQUENCE: 26

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Phe Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Ser Asn Tyr Asp Pro Thr Glu Glu Ile Pro Ala Pro
305                 310                 315                 320
```

-continued

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
            405                 410                 415

Leu Ala Pro Ala Val Ala Pro Thr Phe Pro Gly Glu Gln Leu Leu Phe
        420                 425                 430

Phe Arg Ser Thr Met Pro Gly Cys Ser Gly Tyr Pro Asn Met Asn Leu
    435                 440                 445

Asp Cys Leu Leu Pro Gln Glu Trp Val Gln His Phe Cys Gln Glu Ala
450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
            485                 490                 495

Thr Val Ala His Thr Gly Pro His Asp Leu Val Ile Pro Pro Asn Gly
        500                 505                 510

Tyr Phe Arg Phe Asp Ser Trp Val Asn Gln Phe Tyr Thr Leu Ala Pro
    515                 520                 525

Met Gly Asn Gly Ala Gly Arg Arg Arg Ala Leu
    530                 535

<210> SEQ ID NO 27
<211> LENGTH: 540
<212> TYPE: PRT
<213> ORGANISM: Human norovirus
<220> FEATURE:
<223> OTHER INFORMATION: 2006a strain (Aomori)(G2/4)

<400> SEQUENCE: 27

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
            85                  90                  95

Asn Ser Tyr Ala Gly Gly Phe Glu Val Gln Val Ile Leu Ala Gly Asn
        100                 105                 110

Ala Phe Thr Ala Gly Lys Ile Ile Phe Ala Ala Val Pro Pro Asn Phe
    115                 120                 125

Pro Thr Glu Gly Leu Ser Pro Ser Gln Val Thr Met Phe Pro His Ile
    130                 135                 140

-continued

```
Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
            165                 170                 175

Lys Leu Ile Ala Met Leu Tyr Thr Pro Leu Arg Ala Asn Asn Ala Gly
        180                 185                 190

Asp Asp Val Phe Thr Val Ser Cys Arg Val Leu Thr Arg Pro Ser Pro
    195                 200                 205

Asp Phe Asp Phe Ile Phe Leu Val Pro Pro Thr Val Glu Ser Arg Thr
210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Arg Ile Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asn Tyr Ser Gly Arg Asp Ser His Asn Val
                405                 410                 415

His Leu Ala Pro Ala Val Ala Pro Ser Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Ala Leu
    530                 535                 540

<210> SEQ ID NO 28
<211> LENGTH: 540
<212> TYPE: PRT
```

<213> ORGANISM: Human norovirus
<220> FEATURE:
<223> OTHER INFORMATION: 2006b strain (Saga)(G2/4)

<400> SEQUENCE: 28

```
Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Lys Gly Asp Gly Ser Thr Arg Gly His Lys Ala Thr Val Tyr
            340                 345                 350

Thr Gly Ser Ala Pro Phe Thr Pro Lys Leu Gly Ser Val Gln Phe Ser
        355                 360                 365

Thr Asp Thr Glu Asn Asp Phe Glu Thr His Gln Asn Thr Lys Phe Thr
    370                 375                 380

Pro Val Gly Val Ile Gln Asp Gly Ser Thr Thr His Arg Asn Glu Pro
```

```
                385                 390                 395                 400
        Gln Gln Trp Val Leu Pro Ser Tyr Ser Gly Arg Asn Val His Asn Val
                        405                 410                 415

His Leu Ala Pro Ala Val Ala Pro Thr Phe Pro Gly Glu Gln Leu Leu
                        420                 425                 430

Phe Phe Arg Ser Thr Met Pro Gly Cys Ser Gly Tyr Pro Asn Met Asp
                        435                 440                 445

Leu Asp Cys Leu Leu Pro Gln Glu Trp Val Gln His Phe Tyr Gln Glu
                        450                 455                 460

Ala Ala Pro Ala Gln Ser Asp Val Ala Leu Leu Arg Phe Val Asn Pro
        465                 470                 475                 480

Asp Thr Gly Arg Val Leu Phe Glu Cys Lys Leu His Lys Ser Gly Tyr
                        485                 490                 495

Val Thr Val Ala His Thr Gly Gln His Asp Leu Val Ile Pro Pro Asn
                        500                 505                 510

Gly Tyr Phe Arg Phe Asp Ser Trp Val Asn Gln Phe Tyr Thr Leu Ala
                        515                 520                 525

Pro Met Gly Asn Gly Thr Gly Arg Arg Arg Ala Leu
                        530                 535                 540

<210> SEQ ID NO 29
<211> LENGTH: 540
<212> TYPE: PRT
<213> ORGANISM: Human norovirus
<220> FEATURE:
<223> OTHER INFORMATION: 2007a strain (G2/4)

<400> SEQUENCE: 29

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
```

```
           210                 215                 220
Lys Pro Phe Thr Val Pro Ile Leu Thr Val Glu Glu Met Thr Asn Ser
225                 230                 235                 240

Arg Phe Pro Ile Pro Leu Glu Arg Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Ser Asp Gly Ser Thr Arg Gly His Lys Ala Thr Val Leu
            340                 345                 350

Thr Gly Ser Ala Asp Phe Ala Pro Lys Leu Gly Arg Val Gln Phe Ala
        355                 360                 365

Thr Asp Thr Asp Asn Asp Phe Glu Ser Gly Gln Asn Thr Lys Phe Thr
    370                 375                 380

Pro Val Gly Val Ile Gln Asp Gly Ser Thr Thr His Arg Asn Glu Pro
385                 390                 395                 400

Gln Gln Trp Val Leu Pro Asn Tyr Ser Gly Arg Thr Gly His Asn Val
                405                 410                 415

His Leu Ala Pro Ala Val Ala Pro Thr Tyr Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
530                 535                 540

<210> SEQ ID NO 30
<211> LENGTH: 540
<212> TYPE: PRT
<213> ORGANISM: Human norovirus
<220> FEATURE:
<223> OTHER INFORMATION: 2008a strain (Apeldoorn_317_NL_2007)

<400> SEQUENCE: 30

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
```

```
                35                  40                  45
Asp Pro Trp Ile Arg Asn Asn Phe Val Gln Ala Pro Gly Gly Glu Phe
 50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                 85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Thr Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Ala Asp Gly Ser Thr Arg Gly His Lys Ala Thr Val Tyr
            340                 345                 350

Thr Gly Ser Ala Asp Phe Ala Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460
```

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Thr Gly Arg Arg Ala Leu
            530                 535                 540

<210> SEQ ID NO 31
<211> LENGTH: 540
<212> TYPE: PRT
<213> ORGANISM: Human norovirus
<220> FEATURE:
<223> OTHER INFORMATION: 2008a strain (MiyoshiG2-4)

<400> SEQUENCE: 31

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285
```

```
Asp Val Ala His Ile Ala Gly Ser Arg Asn Tyr Thr Met Asn Leu Ala
        290                 295                 300

Pro Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Lys Gly Asp Gly Ser Thr Arg Gly His Lys Ala Thr Val Tyr
            340                 345                 350

Thr Gly Ser Ala Asp Phe Thr Pro Lys Leu Gly Ser Val Gln Phe Gly
        355                 360                 365

Thr Asp Thr Glu Asn Asp Phe Glu Thr His Gln Asn Thr Lys Phe Thr
370                 375                 380

Pro Val Gly Val Ile Gln Asp Gly Ser Thr Thr His Arg Asn Glu Pro
385                 390                 395                 400

Gln Gln Trp Val Leu Pro Ser Tyr Ser Gly Arg Asn Val His Asn Val
                405                 410                 415

His Leu Ala Pro Ala Val Ala Pro Asn Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Val Gly Asn Gly Thr Gly Arg Arg Arg Val Leu
            530                 535                 540

<210> SEQ ID NO 32
<211> LENGTH: 540
<212> TYPE: PRT
<213> ORGANISM: Human norovirus
<220> FEATURE:
<223> OTHER INFORMATION: 2009a strain (New)

<400> SEQUENCE: 32

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110
```

```
Ala Phe Thr Ala Gly Lys Ile Ile Phe Ala Ala Val Pro Pro Asn Phe
        115                 120                 125
Pro Thr Glu Gly Leu Ser Pro Ser Gln Val Thr Met Phe Pro His Ile
130                 135                 140
Ile Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Pro Thr Ile
                165                 170                 175
Lys Leu Ile Ala Met Leu Tyr Thr Pro Leu Arg Ala Asn Asn Ala Gly
                180                 185                 190
Asp Asp Val Phe Thr Val Ser Cys Arg Val Leu Thr Arg Pro Ser Pro
                195                 200                 205
Asp Phe Asp Phe Ile Phe Leu Val Pro Pro Thr Val Glu Ser Arg Thr
        210                 215                 220
Lys Pro Phe Ser Val Pro Ile Leu Thr Val Glu Met Thr Asn Ser
225                 230                 235                 240
Arg Phe Pro Ile Pro Leu Glu Lys Leu Phe Thr Gly Pro Ser Ser Thr
                245                 250                 255
Phe Val Val Gln Pro Gln Asn Gly Arg Cys Thr Thr Asp Gly Val Leu
                260                 265                 270
Leu Gly Thr Thr Gln Leu Ser Pro Val Asn Ile Cys Thr Phe Arg Gly
        275                 280                 285
Asp Val Thr His Ile Ala Gly Ser Arg Asn Tyr Thr Met Asn Leu Ala
        290                 295                 300
Ser Gln Asn Trp Asn Ser Tyr Asp Pro Thr Glu Ile Pro Ala Pro
305                 310                 315                 320
Leu Gly Thr Pro Asp Phe Val Gly Lys Ile Gln Gly Val Leu Thr Gln
                325                 330                 335
Thr Thr Arg Thr Asp Gly Ser Thr Arg Gly His Lys Ala Thr Val Tyr
                340                 345                 350
Thr Gly Ser Ala Asp Phe Ser Pro Lys Leu Gly Arg Val Gln Phe Ala
        355                 360                 365
Thr Asp Thr Asp Asn Asp Phe Asp Ala Asn Gln Asn Thr Lys Phe Thr
        370                 375                 380
Pro Val Gly Val Ile Gln Asp Gly Gly Thr Ala His Arg Asn Glu Pro
385                 390                 395                 400
Gln Gln Trp Val Leu Pro Ser Tyr Ser Gly Arg Asn Thr His Asn Val
                405                 410                 415
His Leu Ala Pro Ala Val Ala Pro Thr Phe Pro Gly Glu Gln Leu Leu
                420                 425                 430
Phe Phe Arg Ser Thr Met Pro Gly Cys Ser Gly Tyr Pro Asn Met Asp
                435                 440                 445
Leu Asp Cys Leu Leu Pro Gln Glu Trp Val Gln Tyr Phe Tyr Gln Glu
450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
                500                 505                 510
Gly Tyr Phe Arg Phe Asp Ser Trp Val Asn Gln Phe Tyr Thr Leu Ala
                515                 520                 525
```

```
Pro Met Gly Asn Gly Thr Gly Arg Arg Arg Ala Leu
    530                 535                 540
```

<210> SEQ ID NO 33
<211> LENGTH: 540
<212> TYPE: PRT
<213> ORGANISM: Human norovirus
<220> FEATURE:
<223> OTHER INFORMATION: 754 strain (G2/5)

<400> SEQUENCE: 33

```
Met Lys Met Ala Ser Asn Asp Ala Thr Pro Ser Asn Asp Gly Ala Ala
1               5                   10                  15

Gly Leu Val Pro Glu Ser Asn Asn Glu Ala Met Ala Leu Glu Pro Val
            20                  25                  30

Val Gly Ala Ser Leu Ala Ala Pro Val Thr Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Val Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Ile Ile Phe Ala Ala Val Pro Pro Tyr Phe
        115                 120                 125

Pro Val Glu Asn Leu Ser Pro Ser Gln Ile Thr Met Phe Pro His Val
    130                 135                 140

Ile Ile Asp Val Arg Thr Leu Glu Pro Val Leu Leu Pro Met Pro Asp
145                 150                 155                 160

Val Arg Ser Thr Leu Phe His Phe Asn Gln Lys Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Ile Leu Thr Arg Pro Ser Pro
        195                 200                 205

Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240

Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Ser Glu Gln His Met Trp Asn Leu Glu
    290                 295                 300

Ile Thr Asn Leu Asn Gly Thr Gln Phe Asp Pro Thr Asp Val Pro Ala
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350
```

```
Ala Val Val Ala Thr Tyr Ser Asp Lys Tyr Thr Pro Lys Leu Gly Leu
            355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
                420                 425                 430

Phe Phe Arg Ser Tyr Val Pro Leu Lys Gly Gly Phe Gly Asn Pro Ala
            435                 440                 445

Ile Asp Cys Ser Val Pro Gln Glu Trp Val Gln His Phe Tyr Gln Glu
            450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Val Pro Ala Asn
            500                 505                 510

Gly Tyr Phe Arg Phe Asp Ser Trp Val Asn Gln Phe Tyr Ser Leu Ala
            515                 520                 525

Pro Met Gly Thr Gly Asn Gly Arg Arg Arg Val Gln
    530                 535                 540

<210> SEQ ID NO 34
<211> LENGTH: 550
<212> TYPE: PRT
<213> ORGANISM: Human norovirus
<220> FEATURE:
<221> NAME/KEY: MOD_RES
<222> LOCATION: (550)..(550)
<223> OTHER INFORMATION: Any amino acid
<220> FEATURE:
<223> OTHER INFORMATION: 445 strain (G2/6)

<400> SEQUENCE: 34

Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Asp Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160
```

```
Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Ala Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Thr Asp Ser Thr Asp Ser Pro Gln
    290                 295                 300

Arg Ala Arg Asp His Pro Leu His Val Gln Val Lys Asn Leu Asp Gly
305                 310                 315                 320

Thr Gln Tyr Asp Pro Thr Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Pro Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Glu Ser Asn Asp Phe Ile Thr Asn Gln Pro Ile Arg Phe
385                 390                 395                 400

Thr Pro Val Gly Met Gly Asp Asn Asn Trp Arg Gln Trp Glu Leu Pro
                405                 410                 415

Asp Tyr Ser Gly Arg Leu Thr Leu Asn Met Asn Leu Ala Pro Ala Val
            420                 425                 430

Ser Pro Ser Phe Pro Gly Glu Arg Ile Leu Phe Phe Arg Ser Ile Val
        435                 440                 445

Pro Ser Ala Gly Gly Tyr Gly Ser Gly Tyr Ile Asp Cys Leu Ile Pro
    450                 455                 460

Gln Glu Trp Gly Gln His Phe Tyr Gln Glu Ala Ala Pro Ser Gln Ser
465                 470                 475                 480

Ala Val Ala Leu Val Arg Tyr Tyr Asn Pro Asp Thr Gly Arg Asn Ile
                485                 490                 495

Phe Glu Ala Lys Leu His Arg Glu Gly Phe Leu Thr Val Ala Asn Ser
            500                 505                 510

Gly Asn Asn Pro Ile Val Val Pro Pro Asn Gly Tyr Phe Arg Phe Glu
        515                 520                 525

Ala Trp Val Asn Gln Phe Tyr Thr Leu Ala Pro Met Gly Ser Gly Gln
    530                 535                 540

Gly Arg Arg Arg Ala Xaa
545                 550

<210> SEQ ID NO 35
<211> LENGTH: 550
```

<212> TYPE: PRT
<213> ORGANISM: Human norovirus
<220> FEATURE:
<223> OTHER INFORMATION: 7k strain (G2/6)

<400> SEQUENCE: 35

```
Met Lys Met Ala Ser Asn Asp Ala Ala Pro Ser Asn Asp Gly Ala Ala
1               5                   10                  15

Asn Leu Val Pro Glu Ala Asn Asp Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Thr Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Ala Asp Ser Thr Asp Ser Pro Gln
    290                 295                 300

Arg Ala Arg Asn His Pro Leu His Val Gln Val Lys Asn Leu Asp Gly
305                 310                 315                 320

Thr Gln Tyr Asp Pro Thr Asp Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380
```

-continued

```
Ile Lys Ser Gly Ser Asp Asp Phe Asn Thr Asn Gln Pro Ile Arg Phe
385                 390                 395                 400

Thr Pro Val Gly Met Gly Asp Asn Asn Trp Arg Gln Trp Glu Leu Pro
            405                 410                 415

Asp Tyr Ser Gly Arg Leu Thr Leu Asn Met Asn Leu Ala Pro Ala Val
        420                 425                 430

Ser Pro Ser Phe Pro Gly Glu Arg Ile Leu Phe Phe Arg Ser Ile Val
    435                 440                 445

Pro Ser Ala Gly Gly Tyr Gly Ser Gly Tyr Ile Asp Cys Leu Ile Pro
450                 455                 460

Gln Glu Trp Val Gln His Phe Tyr Gln Glu Ala Ala Pro Ser Gln Ser
465                 470                 475                 480

Ala Val Ala Leu Val Arg Tyr Val Asn Pro Asp Thr Gly Arg Asn Ile
            485                 490                 495

Phe Glu Ala Lys Leu His Arg Glu Gly Phe Leu Thr Val Ala Asn Cys
        500                 505                 510

Gly Asn Asn Pro Ile Val Val Pro Pro Asn Gly Tyr Phe Arg Phe Glu
    515                 520                 525

Ala Trp Gly Asn Gln Phe Tyr Thr Leu Ala Pro Met Gly Ser Gly Gln
530                 535                 540

Gly Arg Arg Arg Ala Gln
545                 550

<210> SEQ ID NO 36
<211> LENGTH: 537
<212> TYPE: PRT
<213> ORGANISM: Human norovirus
<220> FEATURE:
<223> OTHER INFORMATION: U25 strain (G2/8)

<400> SEQUENCE: 36

Met Lys Met Ala Ser Asn Asp Ala Ala Pro Ser Asn Asp Gly Ala Ala
1               5                   10                  15

Gly Leu Val Pro Glu Ile Asn His Glu Val Met Ala Ile Glu Pro Val
            20                  25                  30

Ala Gly Ala Ser Leu Ala Ala Pro Val Val Gly Gln Leu Asn Ile Ile
        35                  40                  45

Asp Pro Trp Ile Arg Asn Asn Phe Val Gln Ala Pro Gly Glu Phe
    50                  55                  60

Thr Val Ser Pro Arg Asn Ala Pro Gly Glu Phe Leu Leu Asp Leu Glu
65                  70                  75                  80

Leu Gly Pro Glu Leu Asn Pro Tyr Leu Ala His Leu Ala Arg Met Tyr
            85                  90                  95

Asn Gly His Ala Gly Gly Met Glu Val Gln Ile Val Leu Ala Gly Asn
        100                 105                 110

Ala Phe Thr Ala Gly Lys Ile Leu Phe Ala Val Ile Pro Pro Gly Phe
    115                 120                 125

Pro Tyr Glu Asn Leu Ser Pro Ala Gln Leu Thr Met Cys Pro His Val
130                 135                 140

Val Val Asp Val Arg Gln Leu Glu Pro Ile Leu Leu Pro Met Pro Asp
145                 150                 155                 160

Ile Arg Asn Thr Phe Phe His Tyr Asn Gln Ser Asn Gly Pro Lys Leu
            165                 170                 175

Arg Leu Val Ala Met Leu Tyr Thr Pro Leu Arg Ala Asn Asn Ala Gly
        180                 185                 190
```

```
Glu Asp Val Phe Thr Val Ser Cys Arg Val Leu Thr Arg Pro Ser Pro
            195                 200                 205

Asp Phe Glu Phe Asn Phe Leu Val Pro Pro Ser Val Glu Ser Lys Thr
210                 215                 220

Lys Ala Phe Thr Leu Pro Ile Leu Lys Ile Ser Glu Met Thr Asn Ser
225                 230                 235                 240

Arg Phe Pro Ile Pro Val Asp Gln Met Tyr Thr Ser Arg Asn Glu Asn
                245                 250                 255

Ile Val Val Gln Pro Gln Asn Gly Arg Val Thr Leu Asp Gly Glu Leu
            260                 265                 270

Gln Gly Thr Thr Thr Leu Gln Pro Val Ser Ile Cys Gly Phe Arg Gly
        275                 280                 285

Thr Leu Gln Thr Arg Leu Ala Asp Gln Pro Asn Tyr Thr Tyr Gln Val
    290                 295                 300

His Leu Glu Asn Leu Asp Gly Ser Pro Val Asp Pro Thr Asp Glu Val
305                 310                 315                 320

Pro Ala Pro Leu Gly Thr Pro Asp Phe Gln Ala Gln Leu Phe Gly Val
                325                 330                 335

Ile Ser Gln Arg Ser Ser Asp Asn Ala Thr Arg Ala His Glu Ala Arg
            340                 345                 350

Val Asn Thr Asn Asp Pro Thr Phe Ala Pro Gln Ile Ala Gln Val Arg
        355                 360                 365

Phe Lys Ser Pro Ser Asn Asp Phe Phe Asp Asn Glu Pro Ile Lys Phe
    370                 375                 380

Thr Pro Val Gly Ile Ser Val Asp Ser Gln Asn Ser Tyr Asn Gln Trp
385                 390                 395                 400

Leu Leu Pro Arg Tyr Gly Gly His Leu Thr Asn Asn Thr His Leu Ala
                405                 410                 415

Pro Ser Val Ser Pro Met Phe Pro Gly Glu Gln Ile Leu Phe Phe Arg
            420                 425                 430

Ser Phe Met Pro Gly Ala Ser Gly His Thr Asp Gly Ala Ile Asp Cys
        435                 440                 445

Leu Leu Pro Gln Glu Trp Val Ala His Phe Tyr Gln Glu Ala Ala Thr
    450                 455                 460

Ala Gln Thr Asp Val Ala Leu Ile Arg Phe Val Asn Pro Asp Thr Gly
465                 470                 475                 480

Arg Val Leu Phe Glu Gly Lys Leu His Lys Gln Gly Phe Ile Thr Ile
                485                 490                 495

Ser Asn Ser Gly Asp His Pro Ile Val Met Pro Ala Asn Gly Tyr Phe
            500                 505                 510

Arg Phe Glu Ala Trp Val Asn Gln Phe Tyr Ser Leu Ala Pro Val Gly
        515                 520                 525

Thr Gly Ser Gly Arg Arg Arg Ile Gln
    530                 535

<210> SEQ ID NO 37
<211> LENGTH: 548
<212> TYPE: PRT
<213> ORGANISM: Human norovirus
<220> FEATURE:
<223> OTHER INFORMATION: Viet026 strain (G2/10)

<400> SEQUENCE: 37

Met Lys Met Ala Ser Asn Asp Ala Ala Pro Ser Asn Asp Gly Ala Ala
1               5                   10                  15
```

-continued

Gly Leu Val Pro Glu Ser Asn Asn Glu Val Met Ala Leu Glu Pro Val
            20                  25                  30

Ala Gly Ala Ser Leu Ala Ala Pro Val Thr Gly Gln Thr Asn Ile Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Met Glu Val Gln Ile Met Leu Ala Gly Asn
            100                 105                 110

Ala Phe Thr Ala Gly Lys Leu Ile Phe Ala Ala Val Pro Pro His Phe
        115                 120                 125

Pro Ile Glu Asn Leu Ser Pro Gln Ile Thr Met Phe Pro His Val
    130                 135                 140

Ile Ile Asp Val Arg Thr Leu Glu Pro Val Leu Leu Pro Met Pro Asp
145                 150                 155                 160

Ile Arg Asn Ser Phe Phe His Phe Ile Gln Arg Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Asp Phe Thr Tyr Leu Val Pro Pro Thr Val Glu Ser Lys Ser
    210                 215                 220

Lys Pro Phe Thr Leu Pro Ile Leu Thr Leu Gly Glu Leu Thr Asn Ser
225                 230                 235                 240

Arg Phe Pro Leu Pro Ile Asp Val Leu Tyr Thr Asn Pro Asn Glu Ser
                245                 250                 255

Ala Ile Val Gln Cys Gln Asn Gly Arg Cys Thr Leu Asp Gly Glu Leu
            260                 265                 270

Gln Gly Thr Thr Gln Leu Leu Pro Thr Gly Ile Cys Ala Phe Arg Gly
        275                 280                 285

Lys Val Thr Gln Gln Val Gln Asp Glu His Arg Gly Thr His Trp Asn
290                 295                 300

Met Thr Val Thr Asn Leu Asn Gly Thr Pro Phe Asp Pro Thr Glu Asp
305                 310                 315                 320

Val Pro Ala Pro Leu Gly Thr Pro Asp Phe Ser Gly Gln Ile Tyr Gly
                325                 330                 335

Val Ile Ser Gln Arg Asn Thr Asn Thr Val Pro Gly Glu Gly Asn Leu
            340                 345                 350

Pro Ala Asn Arg Ala His Glu Ala Val Ile Ala Thr Tyr Ser Pro Lys
        355                 360                 365

Phe Thr Pro Lys Leu Gly Asn Ile Gln Phe Ser Thr Trp Glu Thr Gln
    370                 375                 380

Asp Val Ser Ser Gly Gln Pro Thr Lys Phe Thr Pro Val Gly Leu Ala
385                 390                 395                 400

Ser Val Asp Ala Asn Ser His Phe Asp Gln Trp Thr Leu Pro Ser Tyr
                405                 410                 415

Ser Gly Ala Leu Thr Leu Asn Met Asn Leu Ala Pro Ser Val Ala Pro
            420                 425                 430

Val Phe Pro Gly Glu Cys Leu Leu Phe Phe Arg Ser Phe Ile Pro Leu

```
                  435                 440                 445
Lys Gly Gly Tyr Gly Asn Pro Ala Ile Asp Cys Leu Met Pro Gln Glu
    450                 455                 460

Trp Val Gln His Leu Tyr Gln Glu Ser Ala Pro Ser Leu Ser Asp Val
465                 470                 475                 480

Ala Leu Val Arg Tyr Val Asn Pro Glu Thr Gly Arg Thr Leu Phe Glu
                485                 490                 495

Ala Lys Leu His Arg Asn Gly Phe Leu Thr Val Ala Arg Asn Ser Ala
            500                 505                 510

Gly Pro Val Val Ala Pro Thr Asn Gly Tyr Phe Arg Phe Asp Ser Trp
        515                 520                 525

Val Asn Gln Phe Tyr Thr Leu Ala Pro Met Gly Asn Gly Ser Gly Arg
    530                 535                 540

Arg Arg Met Gln
545

<210> SEQ ID NO 38
<211> LENGTH: 535
<212> TYPE: PRT
<213> ORGANISM: Human norovirus
<220> FEATURE:
<223> OTHER INFORMATION: 76 strain (G2/12)

<400> SEQUENCE: 38

Met Lys Met Ala Ser Asn Asp Ala Ala Pro Ser Asn Asp Gly Ala Ala
1               5                  10                  15

Gly Leu Val Pro Glu Ala Asn Asn Glu Thr Met Ala Leu Glu Pro Val
            20                  25                  30

Ala Gly Ala Ser Ile Ala Ala Pro Leu Thr Gly Gln Asn Asn Ile Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Leu Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
```

-continued

```
                    245                 250                 255
Leu Val Val Gln Pro Gln Asn Gly Arg Cys Ala Leu Asp Gly Glu Leu
                260                 265                 270

Gln Gly Thr Thr Gln Leu Leu Pro Thr Ala Ile Cys Ser Phe Arg Gly
            275                 280                 285

Arg Ile Asn Gln Lys Val Ser Gly Glu Asn His Val Trp Asn Met Gln
        290                 295                 300

Val Thr Asn Ile Asn Gly Thr Pro Phe Asp Pro Thr Gly Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Glu Asp Asp Val His Ile Asn Gln Pro Thr Lys Phe
370                 375                 380

Thr Pro Val Gly Leu Phe Glu Asn Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
        435                 440                 445

Pro Gln Glu Trp Ile Gln His Leu Tyr Gln Glu Ser Ala Pro Ser Gln
450                 455                 460

Ser Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Thr Trp Val Asn Gln Phe Tyr Ser Leu Ala Pro Met Gly Thr Gly
        515                 520                 525

Asn Gly Arg Arg Arg Val Gln
530                 535

<210> SEQ ID NO 39
<211> LENGTH: 542
<212> TYPE: PRT
<213> ORGANISM: Human norovirus
<220> FEATURE:
<223> OTHER INFORMATION: 47 strain (G2/14)

<400> SEQUENCE: 39

Met Lys Met Ala Ser Asn Asp Ala Ala Pro Ser Asn Asp Gly Ala Ala
1               5                   10                  15

Ser Leu Val Pro Glu Gly Ile Asn Glu Thr Met Pro Leu Glu Pro Val
                20                  25                  30

Ala Gly Ala Ser Ile Ala Ala Pro Val Ala Gly Gln Thr Asn Ile Ile
            35                  40                  45

Asp Pro Trp Ile Arg Thr Asn Phe Val Gln Ala Pro Asn Gly Glu Phe
        50                  55                  60

Thr Val Ser Pro Arg Asn Ser Pro Gly Glu Ile Leu Leu Asn Leu Glu
```

```
            65                  70                  75                  80
Leu Gly Pro Asp Leu Asn Pro Tyr Leu Ala His Leu Ser Arg Met Tyr
                    85                  90                  95

Asn Gly Tyr Ala Gly Gly Val Glu Val Gln Val Leu Leu Ala Gly Asn
                100                 105                 110

Ala Phe Thr Ala Gly Lys Ile Leu Phe Ala Ala Ile Pro Asn Phe
                115                 120                 125

Leu Val Asp Met Ile Ser Pro Ala Gln Ile Thr Met Leu Pro His Leu
            130                 135                 140

Ile Val Asp Val Arg Thr Leu Glu Pro Ile Met Thr Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
                180                 185                 190

Asp Asp Val Phe Thr Val Ser Cys Arg Val Leu Thr Arg Pro Thr Pro
            195                 200                 205

Asp Phe Glu Phe Ile Tyr Leu Val Pro Pro Ser Val Glu Ser Lys Thr
210                 215                 220

Lys Pro Phe Thr Leu Pro Ile Leu Thr Ile Ser Glu Leu Thr Asn Ser
225                 230                 235                 240

Arg Phe Pro Ile Pro Ile Glu Gln Leu Tyr Thr Ala Pro Asn Glu Thr
                245                 250                 255

Asn Val Val Gln Cys Gln Asn Gly Arg Cys Thr Leu Asp Gly Glu Leu
                260                 265                 270

Gln Gly Thr Thr Gln Leu Leu Ser Ser Ala Val Cys Phe Leu Gln Gly
            275                 280                 285

Arg Thr Val Ala Asp Asn Gly Asp Asn Trp Asp Gln Asn Leu Leu Gln
            290                 295                 300

Leu Thr Tyr Pro Asn Gly Ala Ser Tyr Asp Pro Thr Asp Glu Val Pro
305                 310                 315                 320

Ala Pro Leu Gly Thr Gln Asp Phe Ser Gly Met Leu Tyr Gly Val Leu
                325                 330                 335

Thr Gln Asp Asn Val Asn Val Ser Thr Gly Glu Ala Lys Asn Ala Lys
                340                 345                 350

Gly Ile Tyr Ile Ser Thr Thr Ser Gly Lys Phe Thr Pro Lys Ile Gly
            355                 360                 365

Ser Ile Gly Leu His Ser Ile Thr Glu His Val His Pro Asn Gln Gln
            370                 375                 380

Ser Arg Phe Thr Pro Val Gly Val Ala Val Asp Glu Asn Thr Pro Phe
385                 390                 395                 400

Gln Gln Trp Val Leu Pro His Tyr Ala Gly Ser Leu Ala Leu Asn Thr
                405                 410                 415

Asn Leu Ala Pro Ala Val Ala Arg Leu Ser Leu Val Ser Asn Cys Cys
                420                 425                 430

Ser Ser Gly Pro Val Ser His Val Phe Lys Ala Tyr Arg Gly Gln Asp
            435                 440                 445

Ala Phe Ile Asp Cys Leu Leu Pro Gln Glu Trp Val Asn His Phe Tyr
            450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495
```

```
Gly Phe Ile Thr Val Ser His Thr Gly Ala Tyr Pro Leu Val Val Pro
                500                 505                 510

Pro Asn Gly His Phe Arg Phe Asp Ser Trp Val Asn Gln Phe Tyr Ser
            515                 520                 525

Leu Ala Pro Met Gly Thr Gly Asn Gly Arg Arg Ile Gln
530                 535                 540

<210> SEQ ID NO 40
<211> LENGTH: 540
<212> TYPE: PRT
<213> ORGANISM: Human norovirus
<220> FEATURE:
<223> OTHER INFORMATION: Kamo8 strain (G2/15)

<400> SEQUENCE: 40

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Val Asp Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Ser Asp Gln Arg Met
                165                 170                 175

Arg Leu Ile Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Ser Val Pro Val Leu Thr Leu Glu Leu Thr Asn Ser
225                 230                 235                 240

Arg Phe Pro Val Pro Ile Asp Ala Met Tyr Thr Ser Pro Asn Asp Ser
                245                 250                 255

Ile Val Val Gln Pro Gln Asn Gly Arg Ala Thr Ile Asp Gly Glu Leu
            260                 265                 270

Leu Gly Thr Thr Gln Leu Ile Pro Ser Gly Ile Cys Ser Phe Arg Gly
        275                 280                 285

Lys Ile Thr Thr His Leu Ala Asp Asp Arg His Leu Trp Asn Ile Gln
    290                 295                 300

Val Ser Asn Leu Asn Gly Thr Pro Phe Asp Pro Thr Asp Val Pro
305                 310                 315                 320
```

```
Ala Pro Leu Gly Met Pro Asp Phe Ser Gly Gln Ile Phe Gly Val Val
                325                 330                 335

Ser Gln Arg Asp Thr Gly Thr Asn Pro Ala Asn Arg Ala His Asp Ala
            340                 345                 350

Val Leu Ala Thr Tyr Ser Ala Lys Tyr Thr Pro Lys Leu Gly Ser Val
                355                 360                 365

Gln Ile Gly Thr Trp Asp Thr Glu Asp Leu Leu Glu Arg Gln Pro Val
    370                 375                 380

Lys Phe Thr Pro Val Gly Leu Asn Glu Ile Gly Gln Asp Lys His Phe
385                 390                 395                 400

Asp Gln Trp Val Leu Pro Asn Tyr Ser Gly Ala Leu Gly Leu Asn Met
                405                 410                 415

His Leu Ala Pro Ala Val Ser Pro Leu Phe Pro Gly Glu Arg Leu Leu
                420                 425                 430

Phe Phe Arg Ser Tyr Ile Pro Leu Lys Gly Gly His Gly Asp Pro Phe
            435                 440                 445

Ile Asp Cys Leu Val Pro Gln Glu Trp Ile Gln His Phe Tyr Gln Glu
    450                 455                 460

Ser Ala Pro Ala Gln Ser Ser Val Ala Leu Leu Arg Tyr Val Asn Pro
465                 470                 475                 480

Asp Thr Gly Arg Thr Leu Phe Glu Ala Lys Leu His Lys Glu Gly Phe
                485                 490                 495

Ile Thr Val Ser Ser Thr Glu Asn Arg Pro Val Ile Val Pro Pro Asn
                500                 505                 510

Gly Tyr Phe Arg Phe Asp Ser Trp Val Asn Gln Phe Tyr Ser Leu Ala
            515                 520                 525

Pro Met Gly Thr Gly Asn Gly Arg Arg Arg Val Gln
            530                 535                 540

<210> SEQ ID NO 41
<211> LENGTH: 556
<212> TYPE: PRT
<213> ORGANISM: Human norovirus
<220> FEATURE:
<223> OTHER INFORMATION: Alpha23 strain (G2/17)

<400> SEQUENCE: 41

Met Lys Met Ala Ser Asn Asp Ala Ala Pro Ser Thr Asp Gly Ala Gly
1               5                   10                  15

Asn Leu Val Pro Glu Ser Gln Gln Glu Val Leu Pro Leu Ala Pro Val
                20                  25                  30

Ala Gly Ala Ala Leu Ala Ala Pro Val Val Gly Gln Thr Asn Ile Ile
            35                  40                  45

Asp Pro Trp Ile Lys Glu Asn Phe Val Gln Ala Pro Gln Gly Glu Phe
    50                  55                  60

Thr Val Ser Pro Lys Asn Ser Pro Gly Glu Ile Leu Val Asn Leu Glu
65                  70                  75                  80

Leu Gly Pro Lys Leu Asn Pro Tyr Leu Asp His Leu Ser Arg Met Tyr
                85                  90                  95

Asn Ser Tyr Ala Gly Gly Ile Asp Val Met Val Val Leu Ala Gly Asn
                100                 105                 110

Ala Phe Thr Ala Gly Lys Val Leu Ile Ala Ala Ile Pro Pro Asn Phe
            115                 120                 125

Pro Val Glu Gly Val Ser Ala Ser Gln Ala Thr Gln Phe Pro His Val
    130                 135                 140
```

```
Ile Ile Asp Val Arg Thr Leu Asp Pro Val Arg Leu Pro Leu Pro Asp
145                 150                 155                 160

Val Arg Ser Thr Phe Phe His Tyr Thr Asn Asp Thr Glu Pro Lys Met
            165                 170                 175

Arg Leu Val Ile Trp Leu Tyr Thr Pro Leu Arg Thr Asn Gly Ser Gly
        180                 185                 190

Asp Asp Ser Phe Thr Val Ser Gly Arg Ile Leu Thr Arg Pro Ser Gln
            195                 200                 205

Asp Phe Glu Phe Ala Phe Leu Ile Pro Pro Thr Val Glu Thr Lys Thr
        210                 215                 220

Thr Pro Phe Ser Val Pro Gly Phe Ser Val Gln Glu Met Ser Asn Ser
225                 230                 235                 240

Arg Trp Pro Ala Ala Ile Ser Ala Met Val Val Arg Gly Asn Glu Pro
                245                 250                 255

Gln Val Val Gln Phe Gln Asn Gly Arg Ala His Leu Asp Gly Met Leu
            260                 265                 270

Leu Gly Thr Thr Pro Val Ser Pro Asn Tyr Ile Ala Ser Tyr Arg Gly
        275                 280                 285

Ile Ser Thr Gly Asn Ser Arg Ser Ala Ser Ser Glu Ala Asp Glu Arg
        290                 295                 300

Ala Val Gly Ser Phe Asp Val Trp Val Arg Leu Gln Glu Pro Asp Gly
305                 310                 315                 320

Gln Pro Tyr Asp Ile Phe Gly Lys Gln Pro Ala Pro Ile Gly Thr Pro
                325                 330                 335

Asp Phe Lys Ala Val Ile Val Gly Phe Ala Ala Arg Pro Leu Thr Ser
            340                 345                 350

Gly Ser Tyr Ala Asn Glu Ala Tyr Val Asn Thr Thr Ala Ser Asp Tyr
        355                 360                 365

Ala Pro Ala Thr Gly Asn Met Arg Phe Thr Val Arg Asn Gly Gly Thr
        370                 375                 380

Gly His Ile Ser Ala Asn Lys Tyr Trp Glu Phe Lys Ser Phe Gly Val
385                 390                 395                 400

Glu Gly Glu Arg His Thr Asn Ile Gln Tyr Gln Glu Tyr Glu Leu Pro
                405                 410                 415

Asp Tyr Ser Gly Gln Val Ala Ser Asn His Asn Leu Ala Pro Pro Val
            420                 425                 430

Ala Pro Arg Met Pro Gly Glu Ser Leu Leu Leu Phe Gln Ser Ser Met
        435                 440                 445

Pro Val Trp Asp Asp Gly His Gly Glu Ser Thr Pro Lys Lys Ile His
        450                 455                 460

Cys Leu Leu Pro Gln Glu Phe Ile Gly His Phe Phe Asp Lys Gln Ala
465                 470                 475                 480

Pro Ser Leu Gly Asp Ala Ala Leu Leu Arg Tyr Val Asn Gln Glu Thr
            485                 490                 495

Asn Arg Val Leu Phe Glu Cys Lys Leu Tyr Arg Asp Gly Tyr Ile Thr
            500                 505                 510

Val Ala Ala Ser Ser Gly Leu Leu Asp Phe Pro Leu Asp Gly Phe Phe
        515                 520                 525

Arg Phe Asp Ser Trp Val Ser Ser Phe Tyr Ile Leu Ser Pro Val Gly
        530                 535                 540

Ser Gly Gln Gly Arg Arg Gly Arg Val Arg Phe Gln
545                 550                 555
```